US012697477B2

(12) United States Patent
Ziebol et al.

(10) Patent No.: US 12,697,477 B2
(45) Date of Patent: Aug. 4, 2026

(54) DEVICE FOR DELIVERY OF ANTIMICROBIAL AGENT INTO A MEDICAL DEVICE

(71) Applicant: ICU Medical, Inc., San Clemente, CA (US)

(72) Inventors: Robert J. Ziebol, Shoreview, MN (US); Keith J. Modert, Vadnais Heights, MN (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 18/989,722

(22) Filed: Dec. 20, 2024

(65) Prior Publication Data

US 2025/0121174 A1     Apr. 17, 2025

Related U.S. Application Data

(63) Continuation of application No. 18/494,421, filed on Oct. 25, 2023, now Pat. No. 12,186,520, which is a continuation of application No. 17/710,887, filed on Mar. 31, 2022, now Pat. No. 11,826,539, which is a continuation of application No. 15/850,351, filed on
(Continued)

(51) Int. Cl.
| | |
|---|---|
| *A61M 39/16* | (2006.01) |
| *A61M 1/16* | (2006.01) |
| *A61M 25/00* | (2006.01) |
| *A61M 39/18* | (2006.01) |
(Continued)

(52) U.S. Cl.
CPC ............ *A61M 39/16* (2013.01); *A61M 1/169* (2013.01); *A61M 25/00* (2013.01); *A61M 39/162* (2013.01); *A61M 39/18* (2013.01); *A61M 39/20* (2013.01); *B21D 39/00* (2013.01); *A61M 25/0017* (2013.01); *A61M 2025/0019* (2013.01); *A61M 2025/0056* (2013.01)

(58) Field of Classification Search
CPC ..... A61M 39/16; A61M 39/162; A61M 39/20
See application file for complete search history.

(56) References Cited

U.S. PATENT DOCUMENTS

| | | |
|---|---|---|
| 382,297 A | 5/1888 | Fry |
| 559,697 A | 5/1896 | Tiugti et al. |
(Continued)

FOREIGN PATENT DOCUMENTS

| | | |
|---|---|---|
| AU | 2013 224680 | 9/2016 |
| CA | 2 148 847 | 12/1995 |
(Continued)

OTHER PUBLICATIONS

Machine translation of DE-3515665-C1 (Year: 1986).*
(Continued)

*Primary Examiner* — Kyle A Cook
(74) *Attorney, Agent, or Firm* — Knobbe Martens Olson & Bear LLP

(57) ABSTRACT

A system, method, and article for delivering an antimicrobial agent into the lumen of a trans-dermal catheter are disclosed. In an embodiment, the system comprises an elongate member configured for insertion into a lumen of a catheter, and the elongate member containing an antimicrobial. An antimicrobial agent can be placed on an interior surface of a retaining ring.

20 Claims, 14 Drawing Sheets

Related U.S. Application Data

Dec. 21, 2017, now Pat. No. 11,389,634, which is a continuation of application No. 13/547,572, filed on Jul. 12, 2012, now Pat. No. 9,849,276.

(60) Provisional application No. 61/506,979, filed on Jul. 12, 2011.

(51) Int. Cl.
*A61M 39/20* (2006.01)
*B21D 39/00* (2006.01)

(56) References Cited

U.S. PATENT DOCUMENTS

| | | | |
|---|---|---|---|
| 877,946 A | 2/1908 | Overton |
| 975,939 A | 11/1910 | Edwards et al. |
| 1,445,642 A | 2/1923 | O'Neill |
| 1,793,068 A | 2/1931 | Dickinson |
| 2,098,340 A | 11/1937 | Henahan |
| 2,436,297 A | 2/1948 | Guarnaschelli |
| 2,457,052 A | 12/1948 | Le Clair |
| 2,771,644 A | 11/1956 | Martin |
| 2,842,382 A | 7/1958 | Franck |
| 2,968,497 A | 1/1961 | Treleman |
| 3,127,892 A | 4/1964 | Bellamy, Jr. et al. |
| 3,262,448 A | 7/1966 | Ring et al. |
| 3,270,743 A | 9/1966 | Gingras |
| 3,301,392 A | 1/1967 | Eddingfield |
| 3,304,047 A | 2/1967 | Martin |
| 3,334,860 A | 8/1967 | Bolton, Jr. |
| 3,411,665 A | 11/1968 | Blum |
| 3,484,121 A | 12/1969 | Quinton |
| 3,485,416 A | 12/1969 | Fohrman |
| 3,538,950 A | 11/1970 | Porteners |
| 3,595,241 A | 7/1971 | Sheridan |
| 3,604,582 A | 9/1971 | Boudin |
| 3,707,972 A | 1/1973 | Villari et al. |
| 3,729,031 A | 4/1973 | Baldwin |
| 3,882,858 A | 5/1975 | Klemm |
| 3,977,401 A | 8/1976 | Pike |
| 3,977,517 A | 8/1976 | Kadlecik et al. |
| 3,987,930 A | 10/1976 | Fuson |
| 3,993,066 A | 11/1976 | Virag |
| 4,041,934 A | 8/1977 | Genese |
| 4,046,889 A | 9/1977 | Ondetti et al. |
| 4,052,511 A | 10/1977 | Cushman et al. |
| 4,053,052 A | 10/1977 | Jasper |
| 4,053,651 A | 10/1977 | Ondetti et al. |
| 4,066,067 A | 1/1978 | Micheli |
| 4,076,285 A | 2/1978 | Martinez |
| 4,078,686 A | 3/1978 | Karesh et al. |
| 4,079,738 A | 3/1978 | Dunn et al. |
| 4,095,810 A | 6/1978 | Kulle |
| 4,113,751 A | 9/1978 | Arnold |
| 4,121,585 A | 10/1978 | Becker, Jr. |
| 4,129,571 A | 12/1978 | Ondetti et al. |
| 4,133,441 A | 1/1979 | Mittleman et al. |
| 4,143,853 A | 3/1979 | Abramson |
| 4,150,845 A | 4/1979 | Kopacz et al. |
| 4,154,840 A | 5/1979 | Ondetti et al. |
| 4,154,960 A | 5/1979 | Ondetti et al. |
| 4,192,443 A | 3/1980 | McLaren |
| 4,194,509 A | 3/1980 | Pickering et al. |
| 4,195,632 A | 4/1980 | Parker et al. |
| 4,233,982 A | 11/1980 | Bauer et al. |
| 4,243,035 A | 1/1981 | Barrett |
| 4,245,635 A | 1/1981 | Kontos |
| 4,264,664 A | 4/1981 | Kunz |
| 4,280,632 A | 7/1981 | Yuhara |
| 4,294,370 A | 10/1981 | Toeppen |
| 4,317,446 A | 3/1982 | Ambrosio et al. |
| 4,324,239 A | 4/1982 | Gordon et al. |
| 4,325,368 A | 4/1982 | Kaemmerer |
| 4,331,783 A | 5/1982 | Stoy |
| 4,334,551 A | 6/1982 | Pfister |
| 4,335,756 A | 6/1982 | Sharp et al. |
| 4,337,327 A | 6/1982 | Stoy |
| 4,340,049 A | 7/1982 | Munsch |
| 4,340,052 A | 7/1982 | Dennehey et al. |
| 4,354,490 A | 10/1982 | Rogers |
| 4,369,294 A | 1/1983 | Stoy |
| 4,370,451 A | 1/1983 | Stoy |
| 4,379,458 A | 4/1983 | Bauer et al. |
| 4,379,874 A | 4/1983 | Stoy |
| 4,384,589 A | 5/1983 | Morris |
| 4,387,879 A | 6/1983 | Tauschinski |
| 4,390,016 A | 6/1983 | Riess |
| 4,397,442 A | 8/1983 | Larkin |
| 4,402,691 A | 9/1983 | Rosenthal et al. |
| 4,405,312 A | 9/1983 | Gross et al. |
| 4,417,890 A | 11/1983 | Dennehey et al. |
| 4,420,589 A | 12/1983 | Stoy |
| 4,427,126 A | 1/1984 | Ostrowsky |
| 4,430,073 A | 2/1984 | Bemis et al. |
| 4,432,764 A | 2/1984 | Lopez |
| 4,432,766 A | 2/1984 | Bellotti et al. |
| 4,436,125 A | 3/1984 | Blenkush |
| 4,439,179 A | 3/1984 | Lueders et al. |
| 4,439,184 A | 3/1984 | Wheeler |
| 4,440,207 A | 4/1984 | Genatempo et al. |
| 4,444,310 A | 4/1984 | Odell |
| 4,446,967 A | 5/1984 | Halkyard |
| 4,447,419 A | 5/1984 | Quadro |
| 4,457,749 A | 7/1984 | Bellotti et al. |
| 4,461,368 A | 7/1984 | Plourde |
| 4,461,896 A | 7/1984 | Portlock |
| 4,480,940 A | 11/1984 | Woodruff |
| 4,507,111 A | 3/1985 | Gordon et al. |
| 4,511,359 A | 4/1985 | Vaillancourt |
| 4,534,764 A | 8/1985 | Mittleman et al. |
| 4,538,836 A | 9/1985 | Kruetten |
| 4,559,043 A | 12/1985 | Whitehouse |
| 4,568,675 A | 2/1986 | Bush et al. |
| 4,585,758 A | 4/1986 | Huang et al. |
| 4,602,042 A | 7/1986 | Chantler et al. |
| 4,610,469 A | 9/1986 | Wolff-Mooij |
| 4,619,640 A | 10/1986 | Potolsky et al. |
| 4,623,332 A | 11/1986 | Lindmayer et al. |
| 4,624,664 A | 11/1986 | Peluso et al. |
| 4,626,545 A | 12/1986 | Taub |
| 4,629,159 A | 12/1986 | Wellenstam |
| 4,631,188 A | 12/1986 | Stoy |
| 4,642,091 A | 2/1987 | Richmond |
| 4,660,803 A | 4/1987 | Johnston et al. |
| 4,662,878 A | 5/1987 | Lindmayer |
| 4,666,057 A | 5/1987 | Come et al. |
| 4,666,427 A | 5/1987 | Larsson et al. |
| 4,671,306 A | 6/1987 | Spector |
| 4,671,412 A | 6/1987 | Gatten |
| 4,681,886 A | 7/1987 | Haugwitz et al. |
| 4,692,458 A | 9/1987 | Ryan et al. |
| 4,692,459 A | 9/1987 | Ryan et al. |
| 4,700,744 A | 10/1987 | Rutter et al. |
| 4,703,762 A | 11/1987 | Rathbone et al. |
| 4,705,790 A | 11/1987 | Hubele et al. |
| 4,723,603 A | 2/1988 | Plummer |
| 4,728,075 A | 3/1988 | Paradis |
| 4,728,321 A | 3/1988 | Chen |
| 4,738,668 A | 4/1988 | Bellotti et al. |
| 4,745,950 A | 5/1988 | Mathieu |
| 4,747,502 A | 5/1988 | Luenser |
| 4,748,160 A | 5/1988 | Bennion et al. |
| 4,752,983 A | 6/1988 | Grieshaber |
| 4,769,013 A | 9/1988 | Lorenz et al. |
| 4,774,964 A | 10/1988 | Bonaldo |
| 4,774,965 A | 10/1988 | Rodriguez et al. |
| 4,778,447 A | 10/1988 | Velde et al. |
| 4,781,702 A | 11/1988 | Herrli |
| 4,799,926 A | 1/1989 | Haber |
| 4,804,015 A | 2/1989 | Albinsson |
| 4,808,158 A | 2/1989 | Kreuzer et al. |
| 4,810,241 A | 3/1989 | Rogers |
| 4,811,847 A | 3/1989 | Reif et al. |
| 4,813,933 A | 3/1989 | Turner |

(56)  References Cited

U.S. PATENT DOCUMENTS

| | | | |
|---|---|---|---|
| 4,816,024 A | 3/1989 | Sitar et al. |
| 4,834,271 A | 5/1989 | Litwin |
| 4,862,913 A | 9/1989 | Wildfang |
| 4,874,366 A | 10/1989 | Zdeb et al. |
| 4,883,483 A | 11/1989 | Lindmayer |
| 4,889,255 A | 12/1989 | Schiemann et al. |
| 4,894,056 A | 1/1990 | Bommarito |
| 4,898,580 A | 2/1990 | Crowley |
| 4,915,687 A | 4/1990 | Sivert |
| 4,917,669 A | 4/1990 | Bonaldo |
| 4,919,658 A | 4/1990 | Badia |
| 4,927,019 A | 5/1990 | Haber et al. |
| 4,935,010 A | 6/1990 | Cox et al. |
| 4,941,873 A | 7/1990 | Fischer |
| 4,950,260 A | 8/1990 | Bonaldo |
| 4,957,637 A | 9/1990 | Cornell |
| 4,963,132 A | 10/1990 | Gibson |
| D313,277 S | 12/1990 | Haining |
| D314,050 S | 1/1991 | Sone |
| 4,983,161 A | 1/1991 | Dadson et al. |
| 4,985,017 A | 1/1991 | Theeuwes |
| 4,989,733 A | 2/1991 | Patry |
| 4,991,629 A | 2/1991 | Ernesto et al. |
| 4,997,371 A | 3/1991 | Fischer |
| 4,999,210 A | 3/1991 | Solomon et al. |
| 5,002,964 A | 3/1991 | Loscalzo |
| 5,006,114 A | 4/1991 | Rogers et al. |
| 5,015,238 A | 5/1991 | Solomon et al. |
| 5,019,096 A | 5/1991 | Fox, Jr. et al. |
| 5,021,059 A | 6/1991 | Kensey et al. |
| 5,024,657 A | 6/1991 | Needham et al. |
| 5,025,001 A | 6/1991 | Loscalzo et al. |
| 5,026,359 A | 6/1991 | Burroughs |
| 5,031,622 A | 7/1991 | LaHaye |
| 5,033,961 A | 7/1991 | Kandler et al. |
| 5,047,021 A | 9/1991 | Utterberg |
| 5,049,139 A | 9/1991 | Gilchrist |
| 5,059,186 A | 10/1991 | Yamamoto et al. |
| 5,065,783 A | 11/1991 | Ogle, II |
| 5,070,885 A | 12/1991 | Bonaldo |
| 5,071,411 A | 12/1991 | Hillstead |
| 5,071,413 A | 12/1991 | Utterberg |
| 5,098,385 A | 3/1992 | Walsh |
| 5,108,376 A | 4/1992 | Bonaldo |
| 5,122,123 A | 6/1992 | Vaillancourt |
| 5,127,626 A | 7/1992 | Hilal et al. |
| 5,129,824 A | 7/1992 | Keller |
| 5,139,483 A | 8/1992 | Ryan |
| 5,143,104 A | 9/1992 | Iba et al. |
| 5,147,333 A | 9/1992 | Raines |
| 5,154,703 A | 10/1992 | Bonaldo |
| 5,154,920 A | 10/1992 | Flesher et al. |
| 5,184,742 A | 2/1993 | DeCaprio et al. |
| 5,190,534 A | 3/1993 | Kendell |
| 5,195,957 A | 3/1993 | Tollini |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,205,820 A | 4/1993 | Kriesel |
| 5,205,821 A | 4/1993 | Kruger et al. |
| 5,207,706 A | 5/1993 | Menaker |
| 5,211,634 A | 5/1993 | Vaillancourt |
| 5,212,204 A | 5/1993 | Keefer et al. |
| 5,215,537 A | 6/1993 | Lynn et al. |
| 5,240,675 A | 8/1993 | Wilk et al. |
| 5,242,421 A | 9/1993 | Chan |
| 5,242,425 A | 9/1993 | White et al. |
| 5,246,011 A | 9/1993 | Caillouette |
| 5,250,550 A | 10/1993 | Keefer et al. |
| 5,251,873 A | 10/1993 | Atkinson et al. |
| D342,134 S | 12/1993 | Mongeon |
| 5,269,771 A | 12/1993 | Thomas et al. |
| 5,278,192 A | 1/1994 | Fung et al. |
| 5,281,206 A | 1/1994 | Lopez |
| 5,284,475 A | 2/1994 | Mackal |
| 5,295,657 A | 3/1994 | Atkinson |
| 5,297,310 A | 3/1994 | Cox et al. |
| 5,301,686 A | 4/1994 | Newman |
| 5,304,130 A | 4/1994 | Button |
| 5,306,243 A | 4/1994 | Bonaldo |
| 5,312,377 A | 5/1994 | Dalton |
| 5,324,270 A | 6/1994 | Kayan et al. |
| 5,324,647 A | 6/1994 | Rubens et al. |
| 5,330,235 A | 7/1994 | Wagner et al. |
| 5,330,426 A | 7/1994 | Kriesel et al. |
| 5,330,450 A | 7/1994 | Lopez |
| 5,330,899 A | 7/1994 | Devaughn et al. |
| 5,337,730 A | 8/1994 | Maguire |
| 5,344,414 A | 9/1994 | Lopez et al. |
| 5,352,410 A | 10/1994 | Hansen et al. |
| 5,354,267 A | 10/1994 | Niermann et al. |
| 5,356,396 A | 10/1994 | Wyatt et al. |
| 5,360,413 A | 11/1994 | Leason et al. |
| 5,366,505 A | 11/1994 | Farber |
| 5,366,997 A | 11/1994 | Keefer et al. |
| 5,370,614 A | 12/1994 | Amundson et al. |
| 5,370,636 A | 12/1994 | Von Witzleben |
| 5,370,640 A | 12/1994 | Kolff |
| 5,375,589 A | 12/1994 | Bhatta |
| 5,380,306 A | 1/1995 | Brinon |
| 5,380,758 A | 1/1995 | Stamler et al. |
| 5,391,150 A | 2/1995 | Richmond |
| 5,402,826 A | 4/1995 | Molnar et al. |
| 5,405,331 A | 4/1995 | Behnke et al. |
| 5,405,333 A | 4/1995 | Richmond |
| 5,405,919 A | 4/1995 | Keefer et al. |
| 5,407,807 A | 4/1995 | Markus |
| 5,409,012 A | 4/1995 | Sahatjian |
| 5,411,499 A | 5/1995 | Dudar et al. |
| 5,417,673 A | 5/1995 | Gordon |
| 5,425,465 A | 6/1995 | Healy |
| 5,428,070 A | 6/1995 | Cooke et al. |
| 5,433,330 A | 7/1995 | Yatsko et al. |
| 5,433,705 A | 7/1995 | Giebel et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,464,399 A | 11/1995 | Boettger |
| 5,470,307 A | 11/1995 | Lindall |
| 5,470,327 A | 11/1995 | Helgren et al. |
| 5,471,706 A | 12/1995 | Wallock et al. |
| 5,474,536 A | 12/1995 | Bonaldo |
| 5,480,393 A | 1/1996 | Bommarito |
| 5,485,827 A | 1/1996 | Zapol et al. |
| 5,492,147 A | 2/1996 | Challender et al. |
| 5,496,288 A | 3/1996 | Sweeney |
| 5,501,426 A | 3/1996 | Atkinson et al. |
| 5,507,733 A | 4/1996 | Larkin et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,525,357 A | 6/1996 | Keefer et al. |
| 5,531,695 A | 7/1996 | Swisher |
| 5,533,708 A | 7/1996 | Atkinson et al. |
| 5,533,983 A | 7/1996 | Haining |
| 5,535,785 A | 7/1996 | Werge et al. |
| 5,536,241 A | 7/1996 | Zapol |
| 5,536,258 A | 7/1996 | Folden |
| 5,540,661 A | 7/1996 | Tomisaka et al. |
| 5,545,614 A | 8/1996 | Stamler et al. |
| 5,549,566 A | 8/1996 | Elias et al. |
| 5,549,651 A | 8/1996 | Lynn |
| 5,552,115 A | 9/1996 | Malchesky |
| 5,552,118 A | 9/1996 | Mayer |
| 5,554,127 A | 9/1996 | Crouther et al. |
| 5,554,135 A | 9/1996 | Menyhay |
| 5,555,908 A | 9/1996 | Edwards et al. |
| 5,569,235 A | 10/1996 | Ross et al. |
| 5,573,516 A | 11/1996 | Tyner |

(56) References Cited

U.S. PATENT DOCUMENTS

| | | | |
|---|---|---|---|
| 5,575,769 | A | 11/1996 | Vaillancourt |
| 5,578,059 | A | 11/1996 | Patzer |
| 5,580,530 | A | 12/1996 | Kowatsch et al. |
| 5,584,819 | A | 12/1996 | Kopfer |
| 5,591,137 | A | 1/1997 | Stevens |
| 5,591,143 | A | 1/1997 | Trombley, III et al. |
| 5,597,536 | A | 1/1997 | Mayer |
| 5,599,352 | A | 2/1997 | Dinh et al. |
| 5,605,696 | A | 2/1997 | Eury et al. |
| 5,607,072 | A | 3/1997 | Rigney et al. |
| 5,613,615 | A | 3/1997 | Zeyfang et al. |
| 5,616,130 | A | 4/1997 | Mayer |
| 5,620,088 | A | 4/1997 | Martin et al. |
| 5,620,427 | A | 4/1997 | Werschmidt et al. |
| 5,624,402 | A | 4/1997 | Imbert |
| 5,628,733 | A | 5/1997 | Zinreich et al. |
| RE35,539 | E | 6/1997 | Bonaldo |
| 5,645,538 | A | 7/1997 | Richmond |
| 5,665,077 | A | 9/1997 | Resen et al. |
| 5,674,206 | A | 10/1997 | Allton et al. |
| 5,676,346 | A | 10/1997 | Leinsing |
| 5,685,835 | A | 11/1997 | Brugger |
| 5,685,866 | A | 11/1997 | Lopez |
| 5,685,868 | A | 11/1997 | Lundquist |
| 5,688,253 | A | 11/1997 | Lundquist |
| 5,694,978 | A | 12/1997 | Heilmann et al. |
| 5,699,821 | A | 12/1997 | Paradis |
| 5,700,248 | A | 12/1997 | Lopez |
| 5,702,017 | A | 12/1997 | Goncalves |
| 5,716,339 | A | 2/1998 | Tanaka et al. |
| 5,722,537 | A | 3/1998 | Sigler |
| 5,735,826 | A | 4/1998 | Richmond |
| 5,738,144 | A | 4/1998 | Rogers |
| 5,743,892 | A | 4/1998 | Loh et al. |
| 5,749,861 | A | 5/1998 | Guala et al. |
| 5,763,409 | A | 6/1998 | Bayol et al. |
| 5,770,645 | A | 6/1998 | Stamler et al. |
| 5,776,116 | A | 7/1998 | Lopez |
| 5,782,808 | A | 7/1998 | Folden |
| 5,782,816 | A | 7/1998 | Werschmidt et al. |
| 5,785,693 | A | 7/1998 | Haining |
| 5,792,120 | A | 8/1998 | Menyhay |
| 5,797,887 | A | 8/1998 | Rosen et al. |
| 5,806,831 | A | 9/1998 | Paradis |
| 5,810,792 | A | 9/1998 | Fangrow, Jr. et al. |
| 5,814,024 | A | 9/1998 | Thompson et al. |
| 5,814,666 | A | 9/1998 | Green et al. |
| 5,820,601 | A | 10/1998 | Mayer |
| 5,820,604 | A | 10/1998 | Fox et al. |
| 5,827,244 | A | 10/1998 | Boettger |
| 5,839,715 | A | 11/1998 | Leinsing |
| 5,848,994 | A | 12/1998 | Richmond |
| 5,902,631 | A | 5/1999 | Wang et al. |
| 5,941,857 | A | 8/1999 | Nguyen et al. |
| 5,947,296 | A | 9/1999 | Castora |
| 5,947,954 | A | 9/1999 | Bonaldo |
| 5,951,519 | A | 9/1999 | Utterberg |
| 5,954,957 | A | 9/1999 | Chin-Loy et al. |
| 5,971,972 | A | 10/1999 | Rosenbaum |
| D416,086 | S | 11/1999 | Parris et al. |
| 5,989,229 | A | 11/1999 | Chiappetta |
| 5,994,444 | A | 11/1999 | Trescony |
| 5,996,779 | A | 12/1999 | Klardie et al. |
| 6,029,946 | A | 2/2000 | Doyle |
| 6,036,171 | A | 3/2000 | Weinheimer et al. |
| 6,041,805 | A | 3/2000 | Gydesen et al. |
| 6,045,539 | A | 4/2000 | Menyhay |
| 6,045,623 | A | 4/2000 | Cannon |
| 6,050,978 | A | 4/2000 | Orr et al. |
| 6,059,107 | A | 5/2000 | Nosted et al. |
| 6,063,062 | A | 5/2000 | Paradis |
| 6,068,011 | A | 5/2000 | Paradis |
| 6,068,475 | A | 5/2000 | Stoyka, Jr. et al. |
| 6,068,617 | A | 5/2000 | Richmond |
| 6,071,413 | A | 6/2000 | Dyke |
| 6,079,432 | A | 6/2000 | Paradis |
| 6,087,479 | A | 7/2000 | Stamler et al. |
| 6,093,743 | A | 7/2000 | Lai et al. |
| 6,095,356 | A | 8/2000 | Rits |
| 6,099,519 | A | 8/2000 | Olsen et al. |
| 6,105,812 | A | 8/2000 | Riordan |
| 6,106,502 | A | 8/2000 | Richmond |
| 6,113,068 | A | 9/2000 | Ryan |
| 6,113,572 | A | 9/2000 | Gailey et al. |
| 6,116,468 | A | 9/2000 | Nilson |
| 6,117,114 | A | 9/2000 | Paradis |
| 6,126,640 | A | 10/2000 | Tucker |
| 6,142,446 | A | 11/2000 | Leinsing |
| 6,143,318 | A | 11/2000 | Gilchrist et al. |
| 6,146,363 | A | 11/2000 | Giebel et al. |
| 6,152,913 | A | 11/2000 | Feith et al. |
| 6,158,614 | A | 12/2000 | Haines et al. |
| 6,162,487 | A | 12/2000 | Darouiche |
| 6,170,522 | B1 | 1/2001 | Tanida |
| 6,171,287 | B1 | 1/2001 | Lynn et al. |
| 6,174,539 | B1 | 1/2001 | Stamler et al. |
| 6,179,141 | B1 | 1/2001 | Nakamura |
| 6,183,450 | B1 | 2/2001 | Lois |
| 6,202,870 | B1 | 3/2001 | Pearce |
| 6,202,901 | B1 | 3/2001 | Gerber et al. |
| 6,206,134 | B1 | 3/2001 | Stark et al. |
| 6,206,860 | B1 | 3/2001 | Richmond |
| 6,207,855 | B1 | 3/2001 | Toone et al. |
| 6,217,564 | B1 | 4/2001 | Peters et al. |
| 6,227,391 | B1 | 5/2001 | King |
| 6,232,406 | B1 | 5/2001 | Stoy |
| 6,232,434 | B1 | 5/2001 | Stamler et al. |
| 6,237,800 | B1 | 5/2001 | Barrett et al. |
| 6,242,393 | B1 | 6/2001 | Ishida et al. |
| 6,245,048 | B1 | 6/2001 | Fangrow et al. |
| 6,245,056 | B1 | 6/2001 | Walker et al. |
| 6,248,380 | B1 | 6/2001 | Kocher et al. |
| 6,250,315 | B1 | 6/2001 | Ernster |
| 6,255,277 | B1 | 7/2001 | Stamler et al. |
| 6,267,754 | B1 | 7/2001 | Peters |
| 6,299,132 | B1 | 10/2001 | Weinheimer et al. |
| 6,315,113 | B1 | 11/2001 | Britton et al. |
| 6,315,761 | B1 | 11/2001 | Shcherbina et al. |
| 6,359,167 | B2 | 3/2002 | Toone et al. |
| 6,359,182 | B1 | 3/2002 | Stamler et al. |
| 6,375,231 | B1 | 4/2002 | Picha et al. |
| 6,379,660 | B1 | 4/2002 | Saavedra et al. |
| 6,379,691 | B1 | 4/2002 | Tedeschi et al. |
| 6,394,983 | B1 | 5/2002 | Mayoral et al. |
| 6,402,207 | B1 | 6/2002 | Segal et al. |
| 6,403,759 | B2 | 6/2002 | Stamler et al. |
| 6,409,716 | B1 | 6/2002 | Sahatjian et al. |
| 6,428,520 | B1 | 8/2002 | Lopez |
| 6,431,219 | B1 | 8/2002 | Redler et al. |
| 6,444,318 | B1 | 9/2002 | Guire et al. |
| 6,468,259 | B1 | 10/2002 | Djokic et al. |
| 6,471,978 | B1 | 10/2002 | Stamler et al. |
| 6,488,951 | B2 | 12/2002 | Toone et al. |
| 6,491,965 | B1 | 12/2002 | Berry et al. |
| 6,499,719 | B1 | 12/2002 | Clancy et al. |
| 6,508,792 | B2 | 1/2003 | Szames et al. |
| 6,508,807 | B1 | 1/2003 | Peters |
| 6,538,116 | B2 | 3/2003 | Stamler et al. |
| 6,541,802 | B2 | 4/2003 | Doyle |
| 6,543,745 | B1 | 4/2003 | Enerson |
| 6,550,493 | B2 | 4/2003 | Williamson et al. |
| 6,555,504 | B1 | 4/2003 | Ayai et al. |
| 6,562,781 | B1 | 5/2003 | Berry et al. |
| 6,581,906 | B2 | 6/2003 | Pott et al. |
| 6,583,311 | B2 | 6/2003 | Toone et al. |
| 6,585,691 | B1 | 7/2003 | Vitello |
| 6,595,964 | B2 | 7/2003 | Finley et al. |
| 6,595,981 | B2 | 7/2003 | Huet |
| 6,605,294 | B2 | 8/2003 | Sawhney |
| 6,605,751 | B1 | 8/2003 | Gibbins et al. |
| 6,609,696 | B2 | 8/2003 | Enerson |
| 6,632,199 | B1 | 10/2003 | Tucker et al. |
| 6,634,498 | B2 | 10/2003 | Kayerod et al. |
| 6,656,217 | B1 | 12/2003 | Herzog, Jr. et al. |

(56)        References Cited

U.S. PATENT DOCUMENTS

| | | | |
|---|---|---|---|
| 6,666,852 B2 | 12/2003 | Niedospial, Jr. |
| 6,673,891 B2 | 1/2004 | Stamler et al. |
| 6,679,395 B1 | 1/2004 | Pfefferkorn et al. |
| 6,679,870 B1 | 1/2004 | Finch et al. |
| 6,681,803 B2 | 1/2004 | Taneya et al. |
| 6,685,694 B2 | 2/2004 | Finch et al. |
| 6,692,468 B1 | 2/2004 | Waldenburg |
| 6,695,817 B1 | 2/2004 | Fangrow |
| 6,716,396 B1 | 4/2004 | Anderson |
| 6,722,705 B2 | 4/2004 | Korkor |
| 6,725,492 B2 | 4/2004 | Moore et al. |
| 6,745,998 B2 | 6/2004 | Doyle |
| 6,786,884 B1 | 9/2004 | DeCant, Jr. et al. |
| 6,808,510 B1 | 10/2004 | DiFiore |
| 6,827,766 B2 | 12/2004 | Carnes et al. |
| 6,840,501 B2 | 1/2005 | Doyle |
| 6,871,087 B1 | 3/2005 | Hughes et al. |
| 6,875,205 B2 | 4/2005 | Leinsing |
| 6,875,840 B2 | 4/2005 | Stamler et al. |
| 6,880,706 B2 | 4/2005 | Braconnot et al. |
| 6,887,994 B2 | 5/2005 | Stamler et al. |
| 6,899,315 B2 | 5/2005 | Mailville et al. |
| 6,911,025 B2 | 6/2005 | Miyahar |
| 6,916,051 B2 | 7/2005 | Fisher |
| 6,929,005 B2 | 8/2005 | Sullivan et al. |
| 6,943,035 B1 | 9/2005 | Davies et al. |
| 6,955,669 B2 | 10/2005 | Curutcharry |
| 6,964,406 B2 | 11/2005 | Doyle |
| 7,004,934 B2 | 2/2006 | Vaillancourt |
| 7,015,347 B2 | 3/2006 | Toone et al. |
| 7,030,238 B2 | 4/2006 | Stamler et al. |
| 7,037,302 B2 | 5/2006 | Vaillancourt |
| 7,040,598 B2 | 5/2006 | Raybuck |
| 7,044,441 B2 | 5/2006 | Doyle |
| 7,045,585 B2 | 5/2006 | Berry et al. |
| 7,049,308 B2 | 5/2006 | Stamler et al. |
| 7,052,711 B2 | 5/2006 | West et al. |
| 7,056,308 B2 | 6/2006 | Utterberg |
| 7,067,659 B2 | 6/2006 | Stamler et al. |
| 7,081,109 B2 | 7/2006 | Tighe |
| 7,083,605 B2 | 8/2006 | Miyahara |
| 7,087,709 B2 | 8/2006 | Stamler et al. |
| 7,097,850 B2 | 8/2006 | Chappa et al. |
| 7,100,891 B2 | 9/2006 | Doyle |
| 7,125,396 B2 | 10/2006 | Leinsing et al. |
| 7,140,592 B2 | 11/2006 | Phillips |
| 7,147,625 B2 | 12/2006 | Sarangapani et al. |
| 7,160,272 B1 | 1/2007 | Eyal et al. |
| 7,182,313 B2 | 2/2007 | Doyle |
| 7,195,615 B2 | 3/2007 | Tan |
| 7,198,611 B2 | 4/2007 | Connell et al. |
| 7,244,249 B2 | 7/2007 | Leinsing et al. |
| 7,259,250 B2 | 8/2007 | Stamler et al. |
| 7,279,176 B1 | 10/2007 | West et al. |
| 7,282,186 B2 | 10/2007 | Lake, Jr. et al. |
| 7,306,197 B2 | 12/2007 | Parrino et al. |
| 7,306,198 B2 | 12/2007 | Doyle |
| 7,306,566 B2 | 12/2007 | Raybuck |
| 7,309,326 B2 | 12/2007 | Fangrow, Jr. |
| 7,316,669 B2 | 1/2008 | Ranalletta |
| 7,347,458 B2 | 3/2008 | Rome et al. |
| 7,347,853 B2 | 3/2008 | DiFiore et al. |
| 7,350,764 B2 | 4/2008 | Raybuck |
| 7,361,164 B2 | 4/2008 | Simpson et al. |
| 7,417,109 B2 | 8/2008 | Stamler et al. |
| 7,431,712 B2 | 10/2008 | Kim |
| 7,442,402 B2 | 10/2008 | Chudzik et al. |
| 7,452,349 B2 | 11/2008 | Miyahar |
| 7,485,107 B2 | 2/2009 | DiFiore et al. |
| 7,491,192 B2 | 2/2009 | DiFiore |
| 7,497,484 B2 | 3/2009 | Ziman |
| 7,516,846 B2 | 4/2009 | Hansen |
| 7,588,563 B2 | 9/2009 | Guala |
| 7,611,505 B2 | 11/2009 | Ranalletta et al. |
| 7,614,426 B2 | 11/2009 | Kitani et al. |
| 7,615,034 B2 | 11/2009 | DiFiore |
| 7,625,907 B2 | 12/2009 | Stamler et al. |
| 7,635,344 B2 | 12/2009 | Tennican et al. |
| D607,325 S | 1/2010 | Rogers et al. |
| 7,645,274 B2 | 1/2010 | Whitley |
| 7,651,481 B2 | 1/2010 | Raybuck |
| 7,666,170 B2 | 2/2010 | Guala |
| 7,708,714 B2 | 5/2010 | Connell et al. |
| 7,731,678 B2 | 6/2010 | Tennican et al. |
| 7,731,679 B2 | 6/2010 | Tennican et al. |
| 7,749,189 B2 | 7/2010 | Tennican et al. |
| 7,753,891 B2 | 7/2010 | Tennican et al. |
| 7,758,530 B2 | 7/2010 | DiFiore et al. |
| 7,758,566 B2 | 7/2010 | Simpson et al. |
| 7,762,524 B2 | 7/2010 | Cawthon et al. |
| 7,763,006 B2 | 7/2010 | Tennican |
| 7,766,182 B2 | 8/2010 | Trent et al. |
| 7,766,897 B2 | 8/2010 | Ramsey et al. |
| 7,776,011 B2 | 8/2010 | Tennican et al. |
| 7,780,794 B2 | 8/2010 | Rogers et al. |
| 7,785,616 B2 | 8/2010 | Stamler et al. |
| 7,794,675 B2 | 9/2010 | Lynn |
| 7,799,010 B2 | 9/2010 | Tennican |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,857,793 B2 | 12/2010 | Raulerson et al. |
| 7,922,701 B2 | 4/2011 | Buchman |
| 7,922,711 B2 | 4/2011 | Ranalletta et al. |
| 7,928,079 B2 | 4/2011 | Hrabie et al. |
| 7,938,795 B2 | 5/2011 | DiFiore et al. |
| 7,956,062 B2 | 6/2011 | Stamler et al. |
| 7,959,026 B2 | 6/2011 | Bertani |
| 7,963,565 B2 | 6/2011 | Suter |
| 7,972,137 B2 | 7/2011 | Rosen |
| 7,972,322 B2 | 7/2011 | Tennican |
| 7,981,090 B2 | 7/2011 | Plishka et al. |
| 7,985,302 B2 | 7/2011 | Rogers et al. |
| 7,993,309 B2 | 8/2011 | Schweikert |
| 7,998,134 B2 | 8/2011 | Fangrow et al. |
| 8,034,454 B2 | 10/2011 | Terry |
| 8,065,773 B2 | 11/2011 | Vaillancourt et al. |
| 8,066,670 B2 | 11/2011 | Cluff et al. |
| 8,069,523 B2 | 12/2011 | Vaillancourt et al. |
| 8,113,837 B2 | 2/2012 | Zegarelli |
| 8,146,757 B2 | 4/2012 | Abreu et al. |
| 8,162,899 B2 | 4/2012 | Tennican |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,177,772 B2 | 5/2012 | Christensen et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,252,247 B2 | 8/2012 | Ferlic |
| 8,262,628 B2 | 9/2012 | Fangrow, Jr. |
| 8,262,643 B2 | 9/2012 | Tennican |
| 8,273,303 B2 | 9/2012 | Ferlic et al. |
| 8,281,824 B2 | 10/2012 | Molema et al. |
| 8,328,767 B2 | 12/2012 | Solomon et al. |
| 8,336,152 B2 | 12/2012 | Kerr et al. |
| 8,343,112 B2 | 1/2013 | Solomon et al. |
| 8,361,408 B2 | 1/2013 | Lynn |
| 8,372,045 B2 | 2/2013 | Needle et al. |
| 8,377,040 B2 | 2/2013 | Burkholz et al. |
| 8,414,547 B2 | 4/2013 | DiFiore et al. |
| 8,454,579 B2 | 6/2013 | Fangrow, Jr. |
| 8,480,968 B2 | 7/2013 | Lynn |
| 8,491,546 B2 | 7/2013 | Hoang et al. |
| 8,500,717 B2 | 8/2013 | Becker |
| 8,506,527 B2 | 8/2013 | Carlyon |
| 8,506,538 B2 | 8/2013 | Chelak |
| 8,523,798 B2 | 9/2013 | DiFiore |
| 8,523,831 B2 | 9/2013 | Solomon et al. |
| 8,533,887 B2 | 9/2013 | Hirst |
| 8,545,479 B2 | 10/2013 | Kitani et al. |
| 8,568,371 B2 | 10/2013 | Siopes et al. |
| 8,622,995 B2 | 1/2014 | Ziebol et al. |

(56) References Cited

U.S. PATENT DOCUMENTS

| Patent/Pub No. | | Date | Name |
|---|---|---|---|
| 8,622,996 | B2 | 1/2014 | Ziebol et al. |
| 8,641,684 | B2 | 2/2014 | Utterberg et al. |
| 8,647,308 | B2 | 2/2014 | Solomon et al. |
| 8,647,326 | B2 | 2/2014 | Solomon et al. |
| 8,651,271 | B1 | 2/2014 | Shen |
| 8,740,864 | B2 | 6/2014 | Hoang et al. |
| 8,758,307 | B2 | 6/2014 | Grimm et al. |
| 8,777,504 | B2 | 7/2014 | Shaw et al. |
| 8,791,073 | B2 | 7/2014 | West et al. |
| 8,845,593 | B2 | 9/2014 | Anderson et al. |
| 8,877,231 | B2 | 11/2014 | Rosen |
| 8,910,919 | B2 | 12/2014 | Bonnal et al. |
| 8,920,404 | B2 | 12/2014 | DiFiore et al. |
| 8,968,268 | B2 | 3/2015 | Anderson et al. |
| 8,981,139 | B2 | 3/2015 | Schoenfisch et al. |
| 8,999,073 | B2 | 4/2015 | Rogers et al. |
| 9,022,984 | B2 | 5/2015 | Ziebol et al. |
| 9,072,296 | B2 | 7/2015 | Mills et al. |
| 9,072,868 | B2 | 7/2015 | Ziebol et al. |
| 9,078,992 | B2 | 7/2015 | Ziebol et al. |
| 9,089,680 | B2 | 7/2015 | Ueda et al. |
| 9,101,685 | B2 | 8/2015 | Li et al. |
| 9,149,624 | B2 | 10/2015 | Lewis |
| 9,192,449 | B2 | 11/2015 | Kerr et al. |
| 9,205,248 | B2 | 12/2015 | Wu et al. |
| 9,248,093 | B2 | 2/2016 | Kelley et al. |
| 9,248,229 | B2 | 2/2016 | Devouassoux et al. |
| 9,259,284 | B2 | 2/2016 | Rogers et al. |
| 9,259,535 | B2 | 2/2016 | Anderson et al. |
| 9,283,367 | B2 | 3/2016 | Hoang et al. |
| 9,283,368 | B2 | 3/2016 | Hoang et al. |
| 9,296,525 | B2 | 3/2016 | Murphy et al. |
| 9,302,049 | B2 | 4/2016 | Tekeste |
| 9,320,858 | B2 | 4/2016 | Grimm et al. |
| 9,320,859 | B2 | 4/2016 | Grimm et al. |
| 9,320,860 | B2 | 4/2016 | Grimm et al. |
| 9,352,080 | B2 | 5/2016 | Goodall et al. |
| 9,352,142 | B2 | 5/2016 | Ziebol et al. |
| 9,381,339 | B2 | 7/2016 | Wu et al. |
| 9,399,125 | B2 | 7/2016 | Burkholz |
| 9,527,660 | B2 | 12/2016 | Tennican |
| 9,592,375 | B2 | 3/2017 | Tennican |
| 9,700,676 | B2 | 7/2017 | Anderson et al. |
| 9,700,677 | B2 | 7/2017 | Anderson et al. |
| 9,700,710 | B2 | 7/2017 | Anderson et al. |
| 9,707,348 | B2 | 7/2017 | Anderson et al. |
| 9,707,349 | B2 | 7/2017 | Anderson et al. |
| 9,707,350 | B2 | 7/2017 | Anderson et al. |
| 9,809,355 | B2 | 11/2017 | Solomon et al. |
| 9,849,276 | B2 | 12/2017 | Ziebol et al. |
| 9,867,975 | B2 | 1/2018 | Gardner et al. |
| 9,907,617 | B2 | 3/2018 | Rogers |
| 9,933,094 | B2 | 4/2018 | Fangrow |
| 9,999,471 | B2 | 6/2018 | Rogers et al. |
| 10,016,587 | B2 | 7/2018 | Gardner et al. |
| 10,046,156 | B2 | 8/2018 | Gardner et al. |
| 10,159,829 | B2 | 12/2018 | Ziebol et al. |
| 10,166,381 | B2 | 1/2019 | Gardner et al. |
| 10,195,000 | B2 | 2/2019 | Rogers et al. |
| 10,201,692 | B2 | 2/2019 | Chang |
| 10,328,207 | B2 | 6/2019 | Anderson et al. |
| 10,524,982 | B2 | 1/2020 | Fangrow |
| 10,525,250 | B1 | 1/2020 | Ziebol et al. |
| 10,695,550 | B2 | 6/2020 | Gardner et al. |
| 10,744,316 | B2 | 8/2020 | Fangrow |
| 10,806,919 | B2 | 10/2020 | Gardner et al. |
| 10,821,278 | B2 | 11/2020 | Gardner et al. |
| 11,160,932 | B2 | 11/2021 | Anderson et al. |
| 11,229,746 | B2 | 1/2022 | Anderson et al. |
| 11,351,353 | B2 | 6/2022 | Ziebol et al. |
| 11,389,634 | B2 | 7/2022 | Ziebol et al. |
| 11,400,195 | B2 | 8/2022 | Ziebol et al. |
| 11,433,215 | B2 | 9/2022 | Ziebol et al. |
| 11,497,904 | B2 | 11/2022 | Fangrow et al. |
| 11,517,732 | B2 | 12/2022 | Ziebol et al. |
| 11,517,733 | B2 | 12/2022 | Fangrow |
| 11,534,595 | B2 | 12/2022 | Ziebol et al. |
| 11,541,220 | B2 | 1/2023 | Ziebol et al. |
| 11,541,221 | B2 | 1/2023 | Ziebol et al. |
| 11,559,467 | B2 | 1/2023 | Fangrow |
| 11,684,720 | B2 | 6/2023 | Anderson et al. |
| 11,826,539 | B2 | 11/2023 | Ziebol et al. |
| 11,944,776 | B2 | 4/2024 | Ziebol et al. |
| 11,998,715 | B2 | 6/2024 | Gardner |
| 12,042,640 | B2 | 7/2024 | Anderson et al. |
| 12,076,521 | B2 | 9/2024 | Gardner et al. |
| 12,109,365 | B2 | 10/2024 | Ziebol |
| 12,186,520 | B2 | 1/2025 | Ziebol et al. |
| 12,201,760 | B2 | 1/2025 | Ziebol et al. |
| 12,485,263 | B2 | 12/2025 | Ziebol et al. |
| 12,485,264 | B2 | 12/2025 | Gardner |
| 2002/0077693 | A1 | 6/2002 | Barclay et al. |
| 2002/0082682 | A1 | 6/2002 | Barclay et al. |
| 2002/0098278 | A1 | 7/2002 | Bates et al. |
| 2003/0039697 | A1 | 2/2003 | Zhao et al. |
| 2003/0062376 | A1 | 4/2003 | Sears et al. |
| 2003/0072783 | A1 | 4/2003 | Stamler et al. |
| 2003/0078242 | A1 | 4/2003 | Raad et al. |
| 2003/0153865 | A1 | 8/2003 | Connell et al. |
| 2003/0199835 | A1 | 10/2003 | Leinsing et al. |
| 2003/0208165 | A1 | 11/2003 | Christensen et al. |
| 2004/0034042 | A1 | 2/2004 | Tsuji et al. |
| 2004/0034329 | A1 | 2/2004 | Mankus et al. |
| 2004/0037836 | A1 | 2/2004 | Stamler et al. |
| 2004/0048542 | A1 | 3/2004 | Thomaschefsky et al. |
| 2004/0052689 | A1 | 3/2004 | Yao |
| 2004/0052831 | A1 | 3/2004 | Modak et al. |
| 2004/0073176 | A1 | 4/2004 | Utterberg |
| 2004/0156908 | A1 | 8/2004 | Polaschegg et al. |
| 2004/0210201 | A1 | 10/2004 | Farnan |
| 2004/0215148 | A1 | 10/2004 | Hwang et al. |
| 2004/0247640 | A1 | 12/2004 | Zhao et al. |
| 2004/0249337 | A1 | 12/2004 | DiFiore |
| 2004/0249338 | A1 | 12/2004 | DeCant, Jr. et al. |
| 2004/0258560 | A1 | 12/2004 | Lake, Jr. et al. |
| 2005/0008763 | A1 | 1/2005 | Schachter |
| 2005/0013836 | A1 | 1/2005 | Raad |
| 2005/0015075 | A1 | 1/2005 | Wright et al. |
| 2005/0065479 | A1 | 3/2005 | Schiller et al. |
| 2005/0098527 | A1 | 5/2005 | Yates et al. |
| 2005/0124942 | A1 | 6/2005 | Richmond |
| 2005/0124970 | A1 | 6/2005 | Kunin et al. |
| 2005/0147524 | A1 | 7/2005 | Bousquet |
| 2005/0147525 | A1 | 7/2005 | Bousquet |
| 2005/0148930 | A1 | 7/2005 | Hseih et al. |
| 2005/0152891 | A1 | 7/2005 | Toone et al. |
| 2005/0171493 | A1 | 8/2005 | Nicholls |
| 2005/0197634 | A1 | 9/2005 | Raad et al. |
| 2005/0214185 | A1 | 9/2005 | Castaneda |
| 2005/0220882 | A1 | 10/2005 | Pritchard et al. |
| 2005/0228362 | A1 | 10/2005 | Vaillancourt |
| 2005/0228482 | A1 | 10/2005 | Herzog et al. |
| 2005/0256461 | A1 | 11/2005 | DiFiore et al. |
| 2005/0265958 | A1 | 12/2005 | West et al. |
| 2005/0267421 | A1 | 12/2005 | Wing |
| 2005/0271711 | A1 | 12/2005 | Lynch et al. |
| 2005/0288551 | A1 | 12/2005 | Callister et al. |
| 2006/0004316 | A1 | 1/2006 | DiFiore et al. |
| 2006/0024372 | A1 | 2/2006 | Utterberg et al. |
| 2006/0030827 | A1 | 2/2006 | Raulerson et al. |
| 2006/0058734 | A1 | 3/2006 | Phillips |
| 2006/0096348 | A1 | 5/2006 | DiFiore |
| 2006/0118122 | A1 | 6/2006 | Martens et al. |
| 2006/0129109 | A1 | 6/2006 | Shaw et al. |
| 2006/0142730 | A1 | 6/2006 | Proulx et al. |
| 2006/0149191 | A1 | 7/2006 | DiFiore |
| 2006/0161115 | A1 | 7/2006 | Fangrow |
| 2006/0195117 | A1 | 8/2006 | Rucker et al. |
| 2006/0202146 | A1 | 9/2006 | Doyle |
| 2006/0206178 | A1 | 9/2006 | Kim |
| 2006/0253084 | A1 | 11/2006 | Nordgren |
| 2006/0261076 | A1 | 11/2006 | Anderson |
| 2007/0003603 | A1 | 1/2007 | Karandikar et al. |
| 2007/0088292 | A1 | 4/2007 | Fangrow |

(56)　　　　　References Cited

U.S. PATENT DOCUMENTS

| | | |
|---|---|---|
| 2007/0088293 A1 | 4/2007 | Fangrow |
| 2007/0088294 A1 | 4/2007 | Fangrow |
| 2007/0106205 A1 | 5/2007 | Connell et al. |
| 2007/0112333 A1 | 5/2007 | Hoang et al. |
| 2007/0154621 A1 | 7/2007 | Raad |
| 2007/0156118 A1 | 7/2007 | Ramsey et al. |
| 2007/0167910 A1 | 7/2007 | Tennican et al. |
| 2007/0176117 A1 | 8/2007 | Redmond et al. |
| 2007/0179453 A1 | 8/2007 | Lim et al. |
| 2007/0187353 A1 | 8/2007 | Fox et al. |
| 2007/0202177 A1 | 8/2007 | Hoang |
| 2007/0212381 A1 | 9/2007 | DiFiore et al. |
| 2007/0231315 A1 | 10/2007 | Lichte et al. |
| 2007/0248676 A1 | 10/2007 | Stamler et al. |
| 2007/0249996 A1 | 10/2007 | Tennican et al. |
| 2007/0265578 A1 | 11/2007 | Tennican et al. |
| 2007/0282280 A1 | 12/2007 | Tennican |
| 2007/0287989 A1 | 12/2007 | Crawford et al. |
| 2008/0014005 A1 | 1/2008 | Kitabatake |
| 2008/0027399 A1 | 1/2008 | Harding et al. |
| 2008/0027401 A1 | 1/2008 | Ou-Yang |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0097407 A1 | 4/2008 | Plishka |
| 2008/0103485 A1 | 5/2008 | Kruger |
| 2008/0128646 A1 | 6/2008 | Clawson |
| 2008/0132880 A1 | 6/2008 | Buchman |
| 2008/0147047 A1 | 6/2008 | Davis et al. |
| 2008/0161763 A1 | 7/2008 | Harding et al. |
| 2008/0172007 A1 | 7/2008 | Bousquet |
| 2008/0173651 A1 | 7/2008 | Ping |
| 2008/0177250 A1 | 7/2008 | Howlett et al. |
| 2008/0187460 A1 | 8/2008 | Utterberg et al. |
| 2008/0188791 A1 | 8/2008 | DiFiore et al. |
| 2008/0190485 A1 | 8/2008 | Guala |
| 2008/0193211 A1 | 8/2008 | Burton et al. |
| 2008/0235888 A1 | 10/2008 | Vaillancourt et al. |
| 2008/0262465 A1 | 10/2008 | Zinger et al. |
| 2008/0287920 A1 | 11/2008 | Fangrow et al. |
| 2008/0318333 A1 | 12/2008 | Nielsen et al. |
| 2008/0319423 A1 | 12/2008 | Tanghoj et al. |
| 2009/0008393 A1 | 1/2009 | Howlett et al. |
| 2009/0012426 A1 | 1/2009 | Tennican |
| 2009/0024096 A1 | 1/2009 | Hai et al. |
| 2009/0028750 A1 | 1/2009 | Ryan |
| 2009/0062766 A1* | 3/2009 | Howlett ................ A61M 39/20 |
| | | 604/411 |
| 2009/0093757 A1 | 4/2009 | Tennican |
| 2009/0099529 A1 | 4/2009 | Anderson et al. |
| 2009/0126867 A1 | 5/2009 | Decant, Jr. et al. |
| 2009/0137969 A1 | 5/2009 | Colantonio et al. |
| 2009/0149820 A1 | 6/2009 | DiFiore |
| 2009/0163876 A1 | 6/2009 | Chebator et al. |
| 2009/0205151 A1 | 8/2009 | Fisher et al. |
| 2009/0205656 A1 | 8/2009 | Nishibayashi et al. |
| 2009/0247485 A1 | 10/2009 | Ahmed et al. |
| 2009/0259194 A1 | 10/2009 | Pinedjian et al. |
| 2009/0270832 A1 | 10/2009 | Vancaillie et al. |
| 2009/0293882 A1 | 12/2009 | Terry |
| 2010/0004510 A1 | 1/2010 | Kuroshima |
| 2010/0010086 A1 | 1/2010 | Ash et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0064456 A1 | 3/2010 | Ferlic |
| 2010/0074932 A1 | 3/2010 | Talsma |
| 2010/0106102 A1 | 4/2010 | Ziebol et al. |
| 2010/0106103 A1 | 4/2010 | Ziebol et al. |
| 2010/0137472 A1 | 6/2010 | Ou-Yang |
| 2010/0143427 A1 | 6/2010 | King et al. |
| 2010/0152670 A1 | 6/2010 | Low |

| | | |
|---|---|---|
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0280805 A1 | 11/2010 | DiFiore |
| 2010/0292673 A1 | 11/2010 | Korogi et al. |
| 2010/0292674 A1 | 11/2010 | Jepson et al. |
| 2010/0306938 A1 | 12/2010 | Rogers et al. |
| 2010/0318040 A1 | 12/2010 | Kelley et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0054440 A1 | 3/2011 | Lewis |
| 2011/0062703 A1 | 3/2011 | Lopez |
| 2011/0064512 A1 | 3/2011 | Shaw et al. |
| 2011/0071475 A1 | 3/2011 | Horvath et al. |
| 2011/0082431 A1 | 4/2011 | Burgess et al. |
| 2011/0150958 A1 | 6/2011 | Davis et al. |
| 2011/0175347 A1 | 7/2011 | Okiyama |
| 2011/0184338 A1 | 7/2011 | McKay |
| 2011/0184382 A1 | 7/2011 | Cady |
| 2011/0208128 A1 | 8/2011 | Wu et al. |
| 2011/0232020 A1 | 9/2011 | Rogers et al. |
| 2011/0265825 A1 | 11/2011 | Rogers et al. |
| 2011/0276031 A1 | 11/2011 | Hoang et al. |
| 2011/0277788 A1 | 11/2011 | Rogers et al. |
| 2011/0282302 A1 | 11/2011 | Lopez et al. |
| 2011/0290799 A1 | 12/2011 | Anderson et al. |
| 2011/0314619 A1 | 12/2011 | Schweikert |
| 2012/0022469 A1 | 1/2012 | Albert et al. |
| 2012/0029483 A1 | 2/2012 | Griffith et al. |
| 2012/0031904 A1 | 2/2012 | Kuhn et al. |
| 2012/0039764 A1 | 2/2012 | Solomon et al. |
| 2012/0083730 A1 | 4/2012 | Rush et al. |
| 2012/0083750 A1 | 4/2012 | Sansoucy |
| 2012/0157965 A1 | 6/2012 | Wotton et al. |
| 2012/0191029 A1 | 7/2012 | Hopf et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0220955 A1 | 8/2012 | Maseda et al. |
| 2012/0283693 A1 | 11/2012 | Anderson et al. |
| 2012/0283696 A1 | 11/2012 | Cronenberg et al. |
| 2012/0296284 A1 | 11/2012 | Anderson et al. |
| 2012/0302968 A1 | 11/2012 | Tennican |
| 2012/0302970 A1 | 11/2012 | Tennican |
| 2012/0302997 A1 | 11/2012 | Gardner et al. |
| 2012/0315201 A1 | 12/2012 | Ferlic et al. |
| 2013/0006194 A1 | 1/2013 | Anderson et al. |
| 2013/0023828 A1 | 1/2013 | Anderson et al. |
| 2013/0030414 A1 | 1/2013 | Gardner et al. |
| 2013/0035667 A1 | 2/2013 | Anderson et al. |
| 2013/0039953 A1 | 2/2013 | Dudnyk et al. |
| 2013/0053751 A1 | 2/2013 | Holtham |
| 2013/0072908 A1 | 3/2013 | Solomon et al. |
| 2013/0072909 A1 | 3/2013 | Solomon et al. |
| 2013/0085313 A1 | 4/2013 | Fowler et al. |
| 2013/0085474 A1 | 4/2013 | Charles et al. |
| 2013/0098938 A1 | 4/2013 | Efthimiadis |
| 2013/0102950 A1 | 4/2013 | DiFiore |
| 2013/0123754 A1 | 5/2013 | Solomon et al. |
| 2013/0134161 A1 | 5/2013 | Fogel et al. |
| 2013/0138085 A1 | 5/2013 | Tennican |
| 2013/0144258 A1 | 6/2013 | Ziebol et al. |
| 2013/0150795 A1 | 6/2013 | Snow |
| 2013/0164189 A1 | 6/2013 | Hadden |
| 2013/0171030 A1 | 7/2013 | Ferlic et al. |
| 2013/0183635 A1 | 7/2013 | Wilhoit |
| 2013/0184679 A1 | 7/2013 | Ziebol et al. |
| 2013/0197485 A1 | 8/2013 | Gardner et al. |
| 2013/0204231 A1 | 8/2013 | Ziebol et al. |
| 2013/0255061 A1 | 10/2013 | Burkholz |
| 2013/0274686 A1 | 10/2013 | Ziebol et al. |
| 2014/0042116 A1 | 2/2014 | Shen et al. |
| 2014/0048079 A1 | 2/2014 | Gardner et al. |
| 2014/0052074 A1 | 2/2014 | Tekeste |
| 2014/0101876 A1 | 4/2014 | Rogers et al. |
| 2014/0155868 A1 | 6/2014 | Nelson et al. |

(56) References Cited

U.S. PATENT DOCUMENTS

| | | |
|---|---|---|
| 2014/0227144 A1 | 8/2014 | Liu et al. |
| 2014/0228775 A1 | 8/2014 | Burkholz et al. |
| 2014/0243797 A1 | 8/2014 | Jensen et al. |
| 2014/0261758 A1 | 9/2014 | Wlodarczyk et al. |
| 2014/0336610 A1 | 11/2014 | Michel et al. |
| 2015/0086441 A1 | 3/2015 | She et al. |
| 2015/0141934 A1 | 5/2015 | Gardner et al. |
| 2015/0148287 A1 | 5/2015 | Woo et al. |
| 2015/0157799 A1 | 6/2015 | Chen et al. |
| 2015/0157800 A1 | 6/2015 | Chen et al. |
| 2015/0217106 A1 | 8/2015 | Banik et al. |
| 2015/0258324 A1 | 9/2015 | Chida et al. |
| 2015/0298893 A1 | 10/2015 | Welp |
| 2015/0306367 A1 | 10/2015 | DiFiore |
| 2015/0314119 A1 | 11/2015 | Anderson et al. |
| 2015/0320992 A1 | 11/2015 | Bonnet et al. |
| 2015/0343174 A1 | 12/2015 | Ziebol et al. |
| 2016/0001056 A1 | 1/2016 | Nelson et al. |
| 2016/0001058 A1 | 1/2016 | Ziebol et al. |
| 2016/0015863 A1 | 1/2016 | Gupta et al. |
| 2016/0045629 A1 | 2/2016 | Gardner et al. |
| 2016/0088995 A1 | 3/2016 | Ueda et al. |
| 2016/0089530 A1 | 3/2016 | Sathe |
| 2016/0101223 A1 | 4/2016 | Kelley et al. |
| 2016/0101276 A1 | 4/2016 | Tekeste |
| 2016/0106969 A1 | 4/2016 | Neftel |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0220790 A1 | 8/2016 | Borowicz |
| 2016/0250420 A1 | 9/2016 | Maritan et al. |
| 2016/0354596 A1 | 12/2016 | DiFiore |
| 2017/0020911 A1 | 1/2017 | Berry et al. |
| 2017/0042636 A1 | 2/2017 | Young |
| 2017/0143447 A1 | 5/2017 | Rogers et al. |
| 2017/0182241 A1 | 6/2017 | DiFiore |
| 2017/0203092 A1 | 7/2017 | Ryan et al. |
| 2017/0239443 A1 | 8/2017 | Abitabilo et al. |
| 2018/0028403 A1 | 2/2018 | Fangrow |
| 2018/0085568 A1 | 3/2018 | Drmanovic |
| 2018/0200500 A1 | 7/2018 | Ziebol et al. |
| 2018/0200501 A1 | 7/2018 | Her |
| 2018/0214684 A1 | 8/2018 | Avula et al. |
| 2019/0201681 A1 | 7/2019 | Ziebol et al. |
| 2019/0351211 A1 | 11/2019 | Dombrowski et al. |
| 2020/0069931 A1 | 3/2020 | Fangrow |
| 2020/0085690 A1 | 3/2020 | Fangrow |
| 2020/0121858 A1 | 4/2020 | Anderson et al. |
| 2020/0139037 A1 | 5/2020 | Ziebol et al. |
| 2020/0139101 A1 | 5/2020 | Ziebol et al. |
| 2020/0139102 A1 | 5/2020 | Ziebol et al. |
| 2020/0139103 A1 | 5/2020 | Ziebol et al. |
| 2020/0139104 A1 | 5/2020 | Ziebol et al. |
| 2020/0155794 A1 | 5/2020 | Ziebol et al. |
| 2020/0324102 A1 | 10/2020 | Fangrow |
| 2020/0330741 A1 | 10/2020 | Fangrow et al. |
| 2020/0406020 A1 | 12/2020 | Fangrow |
| 2021/0106805 A1 | 4/2021 | Fangrow |
| 2021/0162194 A1 | 6/2021 | Gardner et al. |
| 2021/0205596 A1 | 7/2021 | Ziebol et al. |
| 2021/0308442 A1 | 10/2021 | Gardner |
| 2022/0226629 A1 | 7/2022 | Ziebol et al. |
| 2022/0288258 A1 | 9/2022 | Gardner |
| 2022/0288376 A1 | 9/2022 | Ziebol |
| 2022/0313977 A1 | 10/2022 | Gugel et al. |
| 2022/0379035 A1 | 12/2022 | Anderson et al. |
| 2022/0387685 A1 | 12/2022 | Ziebol |
| 2022/0401652 A1 | 12/2022 | Anderson et al. |
| 2023/0030414 A1 | 2/2023 | Charrier et al. |
| 2023/0069367 A1 | 3/2023 | Ziebol |
| 2023/0105566 A1 | 4/2023 | Fangrow |
| 2023/0121450 A1 | 4/2023 | Ziebol |
| 2023/0144160 A1 | 5/2023 | Fangrow |
| 2023/0285735 A1 | 9/2023 | Ziebol et al. |
| 2023/0288258 A1 | 9/2023 | Gardner |
| 2024/0050729 A1 | 2/2024 | Ziebol |
| 2024/0050730 A1 | 2/2024 | Fangrow |
| 2024/0139489 A1 | 5/2024 | Ziebol |
| 2024/0216667 A1 | 7/2024 | Ziebol |
| 2025/0025663 A1 | 1/2025 | Ziebol |
| 2025/0099686 A1 | 3/2025 | Anderson |
| 2025/0099732 A1 | 3/2025 | Gardner |
| 2025/0099733 A1 | 3/2025 | Gardner |

FOREIGN PATENT DOCUMENTS

| | | |
|---|---|---|
| CA | 2825217 | 3/2007 |
| CA | 2 769 157 | 2/2011 |
| CA | 2 841 832 | 6/2019 |
| CN | 2402327 Y | 10/2000 |
| CN | 2815392 Y | 9/2006 |
| CN | 201150420 Y | 11/2008 |
| CN | 101405042 | 4/2009 |
| CN | 201519335 U | 7/2010 |
| CN | 102202716 | 9/2011 |
| CN | 102 844 073 A | 12/2012 |
| CN | 103260696 A | 8/2013 |
| CN | 103796704 | 12/2016 |
| CN | 106902402 | 6/2017 |
| CN | 106902405 | 6/2017 |
| CN | 107837428 | 3/2018 |
| DE | 3515665 | 5/1986 |
| DE | 89 06 628 U1 | 9/1989 |
| DE | 43 34 272 | 4/1995 |
| DE | 29617133 | 1/1997 |
| DE | 102007025900 | 12/2008 |
| EP | 0 063 640 | 11/1982 |
| EP | 0 088 341 | 9/1983 |
| EP | 0 108 785 | 5/1984 |
| EP | 0 174 162 | 3/1986 |
| EP | 0 227 219 | 7/1987 |
| EP | 0 237 239 | 9/1987 |
| EP | 0 245 872 | 11/1987 |
| EP | 0 257 485 | 3/1988 |
| EP | 0 639 385 | 2/1995 |
| EP | 0 734 721 | 10/1996 |
| EP | 0 769 265 | 4/1997 |
| EP | 1 061 000 | 10/2000 |
| EP | 1 331 020 | 7/2003 |
| EP | 1 471 011 | 10/2004 |
| EP | 1 442 753 | 2/2007 |
| EP | 1 813 293 | 8/2007 |
| EP | 1 977 714 | 10/2008 |
| EP | 1 312 008 | 4/2009 |
| EP | 2 444 117 | 4/2012 |
| EP | 2 606 930 | 6/2013 |
| EP | 2 671 604 | 12/2013 |
| EP | 2 731 658 | 5/2014 |
| FR | 2 493 149 A | 5/1982 |
| FR | 2 506 162 | 11/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 05-31180 A | 2/1993 |
| JP | 8-81695 A | 3/1996 |
| JP | 09-216661 A | 8/1997 |
| JP | 2000-157630 A | 6/2000 |
| JP | 2002-210011 | 7/2002 |
| JP | 2002-234567 A | 8/2002 |
| JP | 2002-291906 | 10/2002 |
| JP | 2005-218649 | 8/2005 |
| JP | 2006-182663 A | 7/2006 |
| JP | 2006-223583 A | 8/2006 |
| JP | 2009-006148 | 1/2009 |
| JP | 2009-544450 A | 12/2009 |
| JP | 2011-036691 | 2/2011 |
| JP | 2011-528647 | 11/2011 |
| JP | 2012-020125 | 2/2012 |
| JP | 2013-509274 | 3/2013 |

(56)                    References Cited

FOREIGN PATENT DOCUMENTS

| | | |
|---|---|---|
| JP | 2013-520287 | 6/2013 |
| JP | 2013-530794 A | 8/2013 |
| JP | 2014-117461 | 6/2014 |
| JP | 2014-533593 A | 12/2014 |
| JP | 2015-526195 A | 9/2015 |
| JP | 2015-533614 A | 11/2015 |
| JP | 2016-506856 A | 3/2016 |
| JP | 2017-515553 A | 6/2017 |
| JP | 2020-146096 | 9/2020 |
| JP | 2020-146097 | 9/2020 |
| JP | 2013-99665 | 5/2023 |
| RU | 2 246 321 C1 | 2/2005 |
| WO | WO 83/03975 | 11/1983 |
| WO | WO 85/05040 | 11/1985 |
| WO | WO 92/12746 | 8/1992 |
| WO | WO 93/20806 | 10/1993 |
| WO | WO 95/07691 | 3/1995 |
| WO | WO 96/35416 | 11/1996 |
| WO | WO 96/38136 | 12/1996 |
| WO | WO 97/19701 | 6/1997 |
| WO | WO 98/12125 | 3/1998 |
| WO | WO 98/48872 | 11/1998 |
| WO | WO 99/44665 | 9/1999 |
| WO | WO 2001/70199 | 9/2001 |
| WO | WO 2002/05188 | 1/2002 |
| WO | WO 2002/47581 | 6/2002 |
| WO | WO 2002/49544 | 6/2002 |
| WO | WO 2003/015677 | 2/2003 |
| WO | WO 2003/070296 | 8/2003 |
| WO | WO 2004/035129 | 4/2004 |
| WO | WO 2004/112846 | 12/2004 |
| WO | WO 2005/112954 | 12/2005 |
| WO | WO 2005/112974 | 12/2005 |
| WO | WO 2006/007690 | 1/2006 |
| WO | WO 2006/044236 | 4/2006 |
| WO | WO 2006/102756 | 10/2006 |
| WO | WO 2007/008511 | 1/2007 |
| WO | WO 2007/056773 | 5/2007 |
| WO | WO 2007/137056 | 11/2007 |
| WO | WO 2008/014437 | 1/2008 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/060322 | 5/2009 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/011616 | 1/2010 |
| WO | WO 2010/034470 | 4/2010 |
| WO | WO 2010/039171 | 4/2010 |
| WO | WO 2010/062589 | 6/2010 |
| WO | WO 2011/012379 | 2/2011 |
| WO | WO 2011/028722 | 3/2011 |
| WO | WO 2011/053924 | 5/2011 |
| WO | WO 2011/106374 | 9/2011 |
| WO | WO 2011/119021 | 9/2011 |
| WO | WO 2012/009456 | 1/2012 |
| WO | WO 2012/118829 | 9/2012 |
| WO | WO 2012/162006 | 11/2012 |
| WO | WO 2013/009998 | 1/2013 |
| WO | WO 2013/023146 | 2/2013 |
| WO | WO 2013/082180 | 6/2013 |
| WO | WO 2013/184716 | 12/2013 |
| WO | WO 2013/192574 | 12/2013 |
| WO | WO 2014/031628 | 2/2014 |
| WO | WO 2014/074419 | 5/2014 |
| WO | WO 2014/074929 | 5/2014 |
| WO | WO 2014/126867 | 8/2014 |
| WO | WO 2014/140949 | 9/2014 |
| WO | WO 2014/159346 | 10/2014 |
| WO | WO 2015/074087 | 5/2015 |
| WO | WO 2015/119940 | 8/2015 |
| WO | WO 2015/120336 | 8/2015 |
| WO | WO 2015/164129 | 10/2015 |
| WO | WO 2015/164134 | 10/2015 |
| WO | WO 2015/168677 | 11/2015 |
| WO | WO 2015/174953 | 11/2015 |
| WO | WO 2016/025775 | 2/2016 |
| WO | WO 2016/182822 | 11/2016 |
| WO | WO 2017/015047 | 1/2017 |
| WO | WO 2017/127364 | 7/2017 |
| WO | WO 2017/127365 | 7/2017 |
| WO | WO 2018/009653 | 1/2018 |
| WO | WO 2018/071717 | 4/2018 |
| WO | WO 2018/204206 | 11/2018 |
| WO | WO 2018/237090 | 12/2018 |
| WO | WO 2018/237122 | 12/2018 |
| WO | WO 2019/178560 | 9/2019 |
| WO | WO 2019/246472 | 12/2019 |
| WO | WO 2020/097366 | 5/2020 |
| WO | WO 2020/251947 | 12/2020 |
| WO | WO 2022/125474 | 6/2022 |

OTHER PUBLICATIONS

Antibiotic Lock Therapy Guideline, Stanford Hospital and Clinics, Pharmacy Department Policies and Procedures, issued Jun. 2011.
Otto, Mosby's Pocket Guide to Infusion Therapy. Elsevier Health Sciences, 2004. pp. 65-66. Accessed at: http://books.google.com/books?id=j8T14HwWdS4C&lpg=PP1&pg=PP1#v=onepage&f=false (Year: 2004).
"Small-bore connectors for liquids and gases in healthcare applications—Part : Connectors for intravascular or hypodermic applications," ISO 80369-7, Corrected version dated Dec. 1, 2016 (50 pages).
Hospira, "You Work in Neverland," Lifeshield Product Brochure in 2 pages, Published 2009.
Baxter Minicap: Photographs of the Baxter Minicap (Sep. 1, 1998) (4 pages).
Baxter, "Peritoneal Dialysis Patient Connectology," Product Descriptions in 1 page, downloaded Jul. 1, 2011.
Beta Cap II Advertisement from Quinton Instrument Co. (Aug. 1981).
Catheter Connections, "Introducing DualCap," Product Brochure in 1 page, Copyright 2011.
Charney, "Baxter Healthcare InterlinkTM IV Access System" in 1 page, from Handbook of Modern Hospital Safety. Published Mar. 1999.
Clave® Needlefree Connector, icumedical, human connections, 2 page brochure. 2012, M1-1065 Rev. 04.
Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).
Devine, redacted version of letter from David A. Divine, Esq. of Lee & Hayes, dated May 16, 2011 (3 pages).
Devine, redacted version of letter from David A. Divine, Esq. of Lee & Hayes, dated May 27, 2011 (3 pages).
Du. Y, et al. Protein adsorption on polyurethane catheters modified with a novel antithrombin-heparin covalent complex, Journal of Biomedical Materials Research Part A, 2006, 216-225.
Holmer, E. et al. The molecular-weight dependence of the rate-enhancing effect of heparin on theinhibition of thrombin, Factor Xa, Factor IXa, Factor XIa, Factor XIIa and kallikrein by antithrombin, Biochem. J. (1981) 193, 395-400.
Hyprotek, "Port Protek," Product Brochure in 1 page, downloaded Sep. 19, 2011 from http://www.hyprotek.com/products.html.
ICU Medical Antimicrobial Microclave, first sold Jan. 21, 2010, p. 1-2.
ICU Medical SwabPack, top-access bag of disinfecting caps for needlefree connectors, on sale at least as early as Jan. 2012.

(56)　　　　　References Cited

OTHER PUBLICATIONS

Klement, P. et al. Chronic performance of polyurethane catheters covalently coated with ATH complex: A rabbit jugular vein model, Biomaterials, (2006), 27, 5107-5117.

Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).

Photographs of the Baxter Minicap (Sep. 1, 1998) (4 pages).

Thread Check Inc., ISO 80369-7 replaces ISO 594-2:1998€, retrieved 2023; ISO 80369-7 published Oct. 2016, https://www.threadcheck.com/isl-80369/technicalinfo#gref (Year: 2016).

V-Link Luer Activated Device, with VitalShield Protective Coating, 2 page brochure, Baxter Dec. 2009.

U.S. Appl. No. 17/108,887, filed Mar. 31, 2022.

U.S. Appl. No. 16/882,210, filed May 22, 2020.

U.S. Appl. No. 17/832,277, filed Jun. 3, 2022.

Value Plastics, Inc., "Finger Snap Luer Lock Ring (FSLLR)," drawn by Frank Lombardi, May 29, 2011.

Melaiye, et al., "Silver and its application as an antimicrobial agent," Expert Opinion on Therapeutic Patents, 15:2, pp. 125-130, (Year: 2005).

\* cited by examiner

DEVICE FOR DELIVERY OF ANTIMICROBIAL AGENT INTO A MEDICAL DEVICE

This application is a continuation of U.S. Utility application Ser. No. 18/494,421, filed Oct. 25, 2023, which is a continuation of U.S. Utility application Ser. No. 17/710,887, filed Mar. 31, 2022, which is a continuation of U.S. Utility application Ser. No. 15/850,351, filed Dec. 21, 2017 (now U.S. Pat. No. 11,389,634), which is a continuation of U.S. Utility application Ser. No. 13/547,572, filed Jul. 12, 2012 (now U.S. Pat. No. 9,849,276), which claims the benefit of U.S. Provisional Application No. 61/506,979, filed Jul. 12, 2011, the contents of which are herein incorporated by reference.

FIELD OF THE INVENTION

The present invention relates to medical devices for preventing infectious organisms from entering and occupying the lumen of catheters and drainage tubes, and more particularly, to systems, methods, and articles for delivering antimicrobial agents into the lumen and near the entry region (at the proximal end) of catheters and drainage tubes.

BACKGROUND OF THE INVENTION

Hemodialysis catheters allow patients with renal disease to have toxins removed from their bloodstream. Without the use of catheters, many of these patients would not survive. However, long-term hemodialysis catheters have a serious drawback in that a significant percentage of catheters fail due to infection, resulting in elevated mortality rates and large annual healthcare costs associated with treatment. Furthermore, bloodstream infections are a leading cause of death in the United States, and many of those infections are attributable to vascular access devices such as hemodialysis catheters. The mortality rate associated with such infections is considerable.

Therefore, a need exists for a manner in which infections relating to long-term hemodialysis catheters can be reduced.

SUMMARY OF THE INVENTION

The present application is directed, in part, to a device for delivering an antimicrobial agent into the lumen of a transdermal catheter. The device comprises an elongate member configured for insertion into the proximal end of a catheter and an antimicrobial composition positioned to be delivered into the catheter. At least a portion of the antimicrobial composition is delivered to the exterior of the proximal end of the catheter upon insertion of the elongate member into the proximal end of the catheter.

The application is also directed to a device for delivering an antimicrobial agent into the lumen of a trans-dermal catheter, the device comprising a capping member configured for placement over the proximal end of a catheter; and an antimicrobial composition positioned on the interior of the capping member.

The application is further directed to a method of applying an antimicrobial to the proximal end of a trans-dermal catheter. The method includes providing a transdermal catheter; filling at least a portion of the proximal end of the transdermal catheter with a lock solution; clamping the transdermal catheter near its proximal end to restrict flow of the lock solution into the distal end of the transdermal catheter; and inserting an elongate member into the proximal end of the transdermal catheter such that the elongate member sufficiently displaces lock solution so as to have the lock solution flow from the proximal end of the catheter. The elongate member includes or incorporates an antimicrobial material.

This summary is not intended to be limiting of the invention. The invention is further described in the following detailed description and claims.

BRIEF DESCRIPTION OF THE DRAWINGS

The invention may be more completely understood in connection with the following drawings, in which.

US 12,697,477 B2

3

Figure 9:
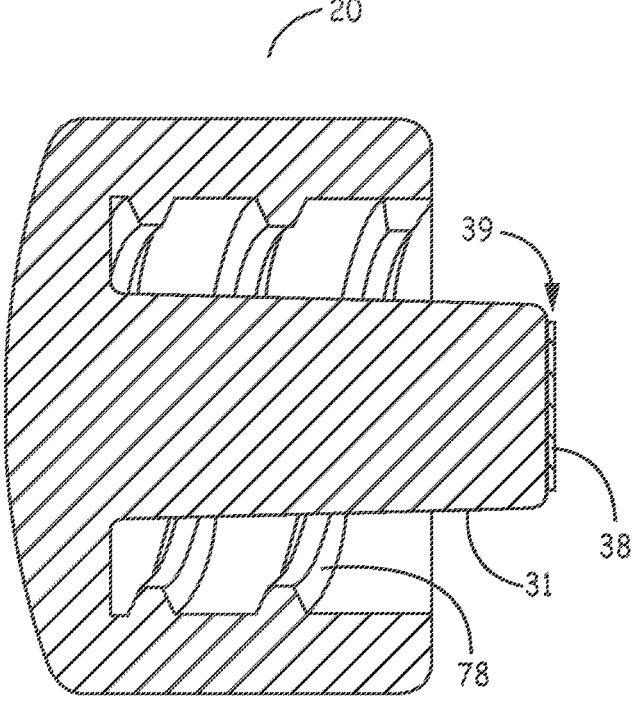

FIG. 9 is a side cross-section view of a cap not containing an elongate member made in accordance with an implementation of the invention.

Figure 10A:
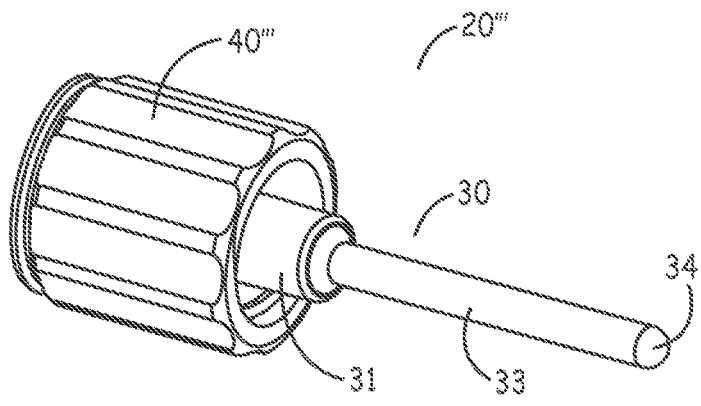

FIG. 10A is a perspective view, looking from the distal end of a cap, made in accordance with a preferred implementation of the invention.

Figure 10B:
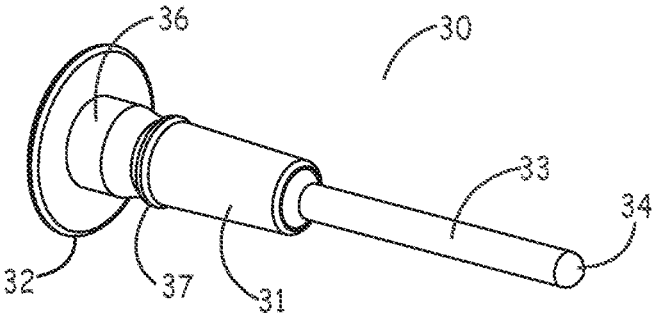

FIG. 10B is a perspective view, looking from the distal end of an insert, made in accordance with a preferred implementation of the invention.

Figure 10C:
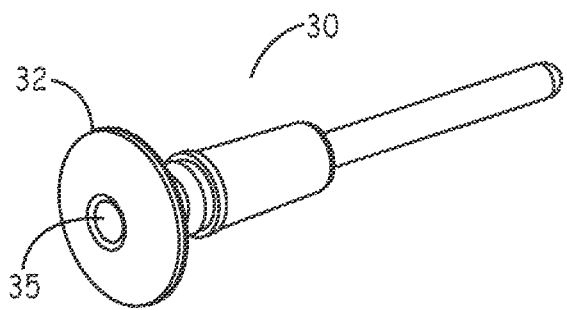

FIG. 10C is a perspective view, looking from the proximal end of an insert, made in accordance with a preferred implementation of the invention.

Figure 10D:
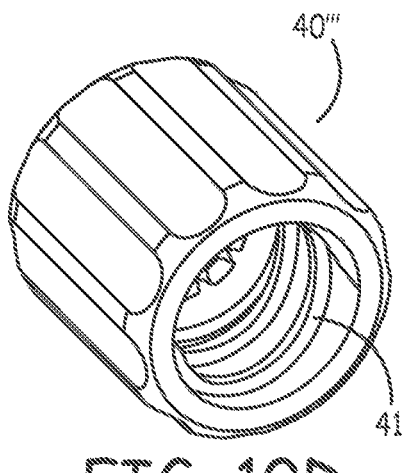

FIG. 10D is a perspective view, looking from the distal end of a retaining ring, made in accordance with a preferred implementation of the invention.

Figure 10E:
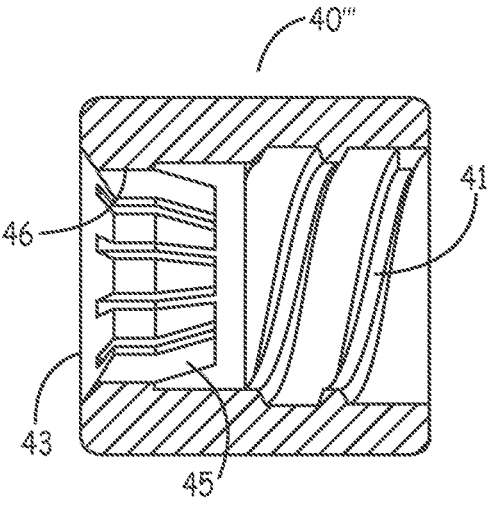

FIG. 10E is a side section view of a retaining ring made in accordance with a preferred implementation of the invention.

Figure 10F:
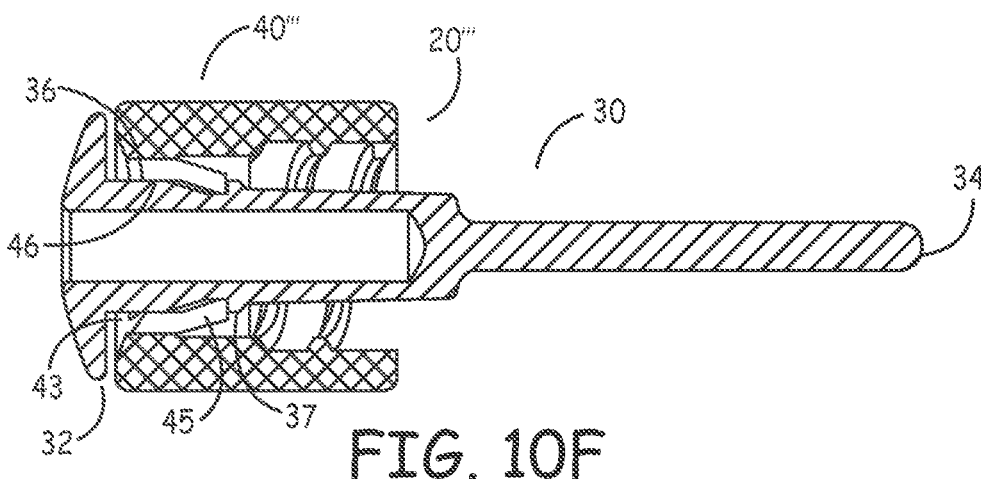

FIG. 10F is a side cross section view of a cap made in accordance with a preferred implementation of the invention.

Figure 11:
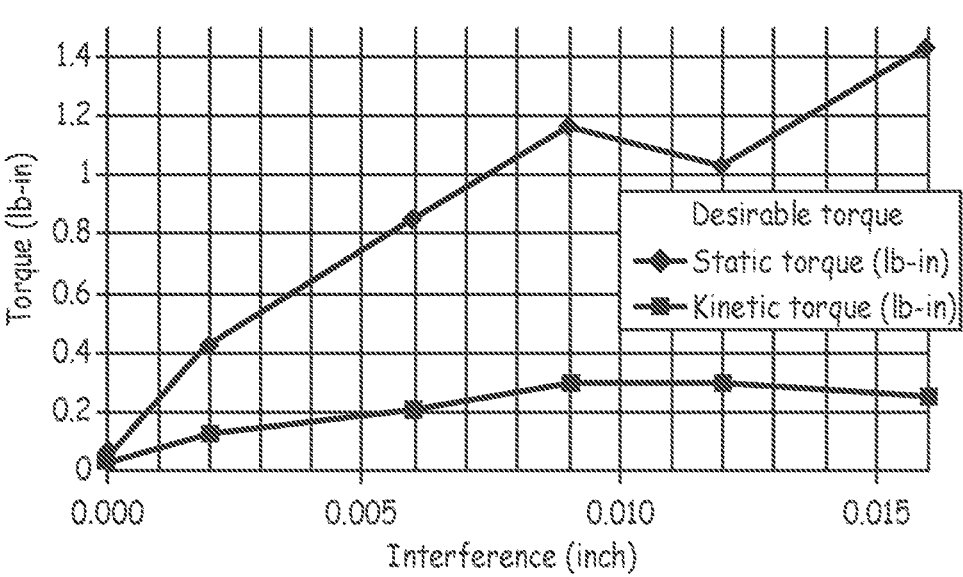

FIG. 11 is a table showing the effect of interference between a retaining ring and shoulder upon ring-insert torque.

Figure 12:
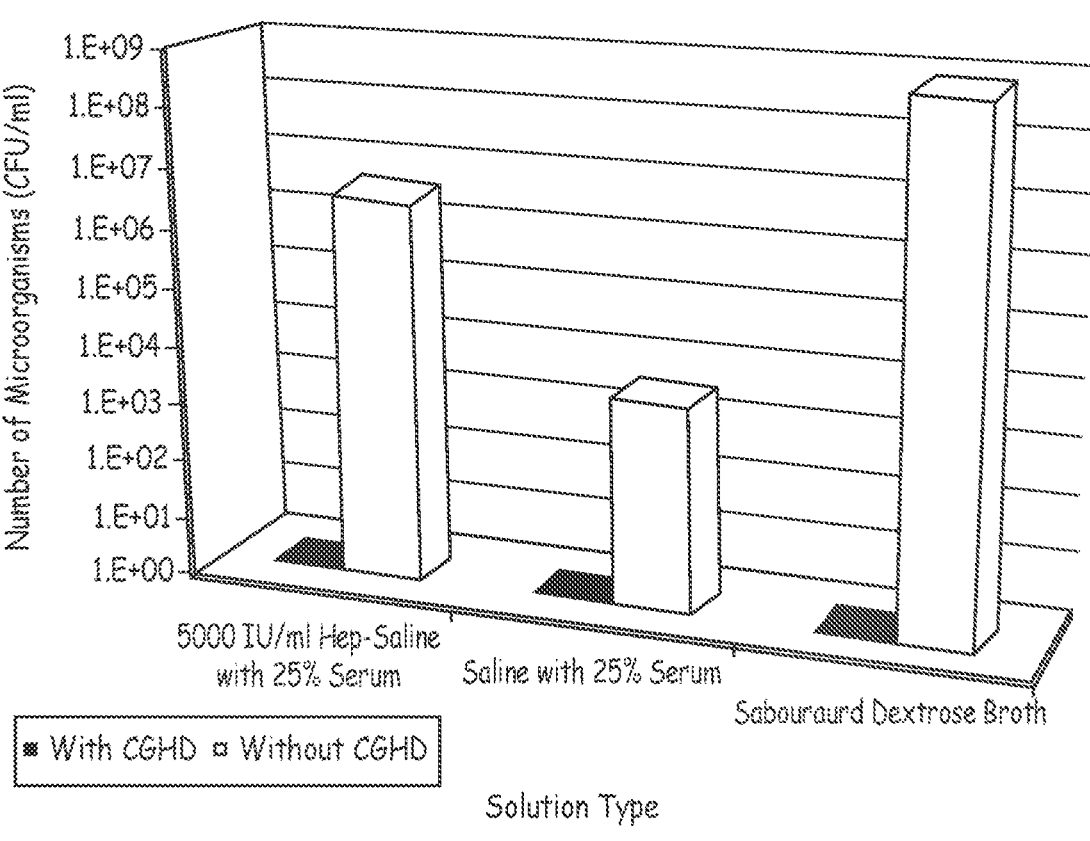

FIG. 12 shows concentration of microbes grown in various catheter conditions.

Figure 13:
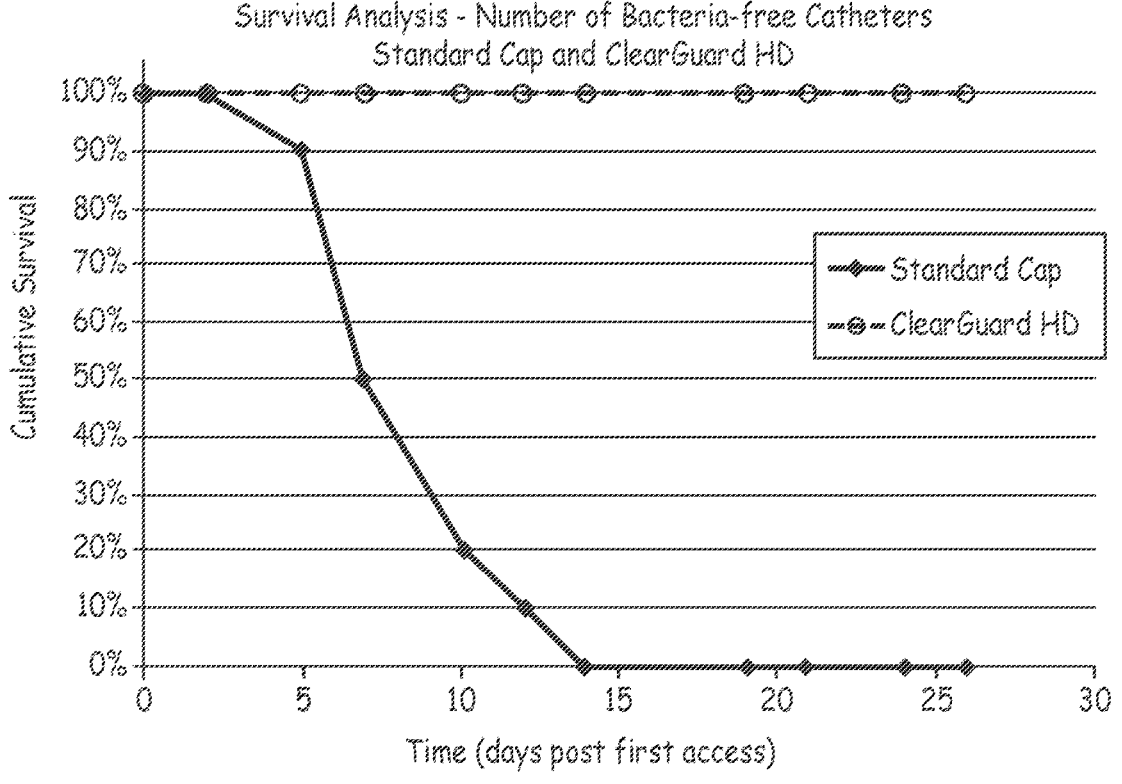

FIG. 13 shows a chart of survival analysis of bacteria-free catheters under various conditions.

DETAILED DESCRIPTION OF THE
PREFERRED EMBODIMENT

The present invention relates to devices, systems, and methods for treating, preventing and eliminating infectious organisms in medical devices, such as catheters and drainage tubes, and preventing the organisms from entering the bloodstream. The devices, systems, and methods deliver antimicrobial agents into the lumen and near the entry region of catheters and drainage tubes. The following detailed description presents a description of certain specific embodiments to assist in understanding the claims. However, one may practice the present invention in a multitude of different embodiments as defined and covered by the claims.

The present invention includes, in certain implementations, methods and devices for preventing organism proliferation and biofilm formation in catheters so that organisms aren't able to exit the catheter and enter the bloodstream of a patient. The device and system prevents, or reduces the number of, organisms reaching the bloodstream by employing any or all of the following three prevention methods: 1) physically blocking migration of organisms outside the catheter, 2) killing organisms along the threads, end face and luer connector at the proximal end (outside of the body) of the catheter using an antimicrobial, and/or 3) killing organisms within a confined region of the catheter using an antimicrobial agent and/or a physical barrier in the catheter lumen. A fourth mode of action, scrubbing the catheter wall (to physically remove organisms adhered to the catheter's proximal end (thread and/or end face) and/or the interior wall section upon removing the cap from the catheter) may also be used in conjunction with the other methods and devices, or independently in certain implementations.

In a first aspect, the present invention includes an organism barrier at the external end of the catheter, also referred to herein as the proximal end of the catheter. This barrier provides a seal to keep organisms from reaching the end face and luer portions of the connector on a catheter. This can be accomplished, for example, by using either of the following features: First, placing an elastomeric flap or gasket (i.e., silicone, neoprene, polyurethane, etc.) that is positioned at the end of the cap's connector or, alternatively, along the inner wall of the cap's locking-ring. The flap preferably makes a fluid tight seal against the outer wall of the catheter's connector, thereby decreasing the likelihood of microbial incursion and preventing microbial growth. Second, placing foam, either closed cell or open cell that preferably contains an antimicrobial, along the inner wall of the cap's retaining ring and/or at the most proximal location in the cap such that it will abut and seal against the proximal end of the catheter's connector surface (also called the end face).

An embodiment using an antimicrobial agent along the cap's tread region, but not containing an organism barrier, can also be used to reduce the number of organisms that can enter the catheter. This reduction in the number of organisms that can enter the catheter is accomplished by killing organisms within the tread and end face region. The cap is optionally designed to transfer antimicrobial agent from the cap to the catheter threads. This is accomplished by displacing fluid from the catheter into the thread region of the connector. The elongate member and luer, when entering the catheter, displace the catheter's fluid, causing the fluid to flow out into the thread region between the connector and the cap.

Antimicrobial agent dissolves in the fluid, causing the fluid to become saturated with antimicrobial agent. The antimicrobial fluid produces an effective antiseptic region, killing organisms on the connector. Furthermore, as the fluid dries, antimicrobial precipitates from the fluid and is deposited onto the catheter threads and end face. This process is repeated every time a new cap is placed onto the catheter, thus replenishing the antimicrobial agent on the catheter's proximal region with every new cap.

In a second aspect, the invention is directed to adding of an antimicrobial along a luer connector. This can be accomplished, for example, by coating a male luer connector with various antimicrobial agents.

In a third aspect, the invention is directed to an antimicrobial agent inside the catheter. The antimicrobial can be delivered as a coating that elutes from a coated elongate member, that is coated on (or impregnated into) a elongate member (such as 250 µg of chlorhexidine acetate in a layer approximately 2 µm thick along a 17 mm long×1.9 mm diameter elongate member/rod). The elongate member has the added benefit of displacing fluid from within the catheter as it is inserted, thereby transferring the solution to the outer proximal region of the catheter connector (end face and treads). Antimicrobial agent from the cap dissolves into the displaced fluid, and thereby disinfecting the proximal end of the connector. Furthermore, when the fluid dries, it deposits a coating of chlorhexidine acetate or other appropriate antimicrobial on the connector as described above. As an alternative to using the elongate member, the chlorhexidine acetate or other antimicrobial agent may be delivered by a coating on a luer tip (such as 250 µg of chlorhexidine acetate in a layer that is approximately 20 µm thick). A minimum of 10 µg of chlorhexidine acetate on the elongate member is effective for many organisms in some implementations. A desirable minimum of greater than 100 µg is effective for most organisms, and a further desired minimum of 250 µg is highly effective against all of the major organisms.

Types of antimicrobial agent can include chlorhexidine base, chlorhexidine acetate, chlorhexidine gluconate, EDTA, silver sulfadiazine, or Taurolidine; or combinations thereof. Other antimicrobial agents may also be used. Chlorhexidine acetate is preferred because it has a long history of human use, with a well understood safety and efficacy profile.

Typically these methods are also used in conjunction with confinement of the antimicrobial in the catheter, such as by relying on a catheter clamp to confine the antimicrobial agent in a portion of the proximal end of the catheter (that portion of the catheter outside of a patient and in particular that portion nearest the connector on the catheter by which fluids enter and leave the catheter). Extension tube clamps are part of each hemodialysis catheter and are currently used to confine lock solutions that are used to help ensure catheter patency. Using the existing clamp methodology, the risk of air embolus and lock solution entering the patient is very small and consistent with the current state of the art for conducting hemodialysis procedures. In other medical devices, such as catheters that do not possess catheter clamps, a swellable cap tip or other confinement technique, such as those described in United States patent application publication number US 2010/0106103 A1, may be used.

Organism mechanical removal can also be utilized. In this regard, a portion of the elongate member can scrap the catheter wall upon removal, such as by having ribs incorporated into the elongate member. In some implementations, after placing the elongate member into the catheter, anisotropic swelling moves ribs (or other projections) against wall, which provides a tighter fit against the wall after swelling and further promotes mechanical removal of the organisms. Also, it is possible for the tip of the elongate member to swell (or other portions such as ribs to swell), or swelling along the length of the elongate member. Preferably the elongate member's unswollen diameter is smaller than the catheter lumen when the elongate member is being inserted, but swells to conform to the inner shape (or larger) of the catheter lumen to enhance the mechanical removal of the organisms during removal. Various polyurethanes or other material may be used to produce suitable anisotropic swelling and mechanical stability; more specifically, Lubrizol 1065D is suitable for a non-swelling elongate member and TG-500 is suitable for an anisotropic swelling (or isotropic swelling) tip which may be bonded with each other using heat bonding or other suitable methods.

An embodiment of the invention, herein referred to as "the cap", contains an elongate member that can be inserted into a medical device, such as a catheter or a drainage tube, for the prevention and treatment of infectious organisms within the medical device and in proximity to the elongate member, and further prevents the migration of infectious organisms into the body by providing an antimicrobial and/or physical barrier. For the sake of simplicity, the term "catheter" is used for all medical devices in which the present invention can be inserted and used to treat, prevent, and eliminate infectious organisms. The cap may be removed from the catheter to allow the catheter to be used in a dialysis procedure or other procedure. After the procedure is complete, a new cap may be used to seal and protect the catheter. The removal of one cap and the replacement with a new cap may be repeated an indefinite number of times. With each new cap, the antimicrobial agent inside and outside of the catheter is reestablished. Another aspect of the invention is that antimicrobial agent is transferred from the cap to the catheter with each use.

An example embodiment includes an elongated rod comprising a suitable material into which an antimicrobial agent has been incorporated. The term "antimicrobial," as used here, includes any substance or substances that kills or inhibits the growth of organisms such as bacteria, fungi, protozoa, viruses, etc. It should also be noted that there can be one or more antimicrobial agents used. Therefore, throughout this document, antimicrobial agent refers to one or more antimicrobial agents. While the invention may be used in a variety of medical devices, a catheter, and more specifically a long-term hemodialysis catheter, will be used to describe the use of the invention. The use of these examples is not meant to confine or limit the use of the invention in other types of catheters or medical devices, such as peritoneal dialysis catheters, urinary catheters, PICC lines, central venous catheters, feeding tubes and drainage catheters.

One useful application of the invention is in preventing infections in people with hemodialysis catheters. The present invention prevents or eliminates infectious organisms on connector and the luminal wall of a catheter by providing a means for the prolonged presence of an antimicrobial agent and/or providing a means for periodically scrubbing the luminal wall of the catheter to remove the biofilm in which infectious organisms proliferate.

Competing methods for preventing, eliminating, and treating infectious organisms in the lumen of a catheter are in limited use. One method uses an antimicrobial coating on or in the internal wall of the catheter. The issues that have precluded widespread use include the antimicrobial coating eventually wearing off, losing potency, or becoming covered with blood products, rendering the coating ineffective. When antibiotics are used as the antimicrobial agent, there is an additional concern regarding the emergence of resistant organisms to antibiotics and the risk of anaphylaxis to the antibiotics. Another method for treating infectious organisms in the lumen is the use of an antibiotic or antimicrobial liquid, known as a locking agent or locking solution. In this method, an antimicrobial fluid is injected into the catheter, and a cap is attached to the hub of the catheter to prevent the fluid from leaking out of the catheter and to prevent infectious organisms from entering into the lumen.

One issue precluding widespread use of this method is concern for the emergence of resistant organisms if an antibiotic agent is used. This concern may be virtually eliminated, however, by using a non-antibiotic antimicrobial, such as taurolidine. Another issue when dialysis catheters are filled with locking solutions is that the locking solution spills into the bloodstream. This occurs for two reasons. First, when the catheter is filled with a volume equal to the catheter volume, a significant portion of the fluid leaks out due to the nature of the laminar flow profile in the catheter. Second, blood flow by the tip/distal end results in the injected catheter locking solution being pulled out due to the Venturi effect, and density differences between the lock solution result in spillage of the solution into the bloodstream. It has been reported that 60% or more of the locking solution is spilled into the bloodstream in the first few hours after instillation. Accidental overdosing, either from injecting too much volume or too high of concentration of the locking solution, can cause additional spillage into the bloodstream. Spillage has resulted in adverse events, including death. For instance, spillage has resulted in death from transient hypocalcemia when a citrate solution was used. In addition, other adverse events may occur as some types of locking solutions may build up in the body.

In the case of using the cap with dialysis catheters, the present invention is designed to be replaced regularly after each dialysis session, approximately three times per week. This replenishes the antimicrobial agent with each replacement, resulting in a consistent and high concentration of antimicrobial agent present within and upon the catheter on an ongoing basis resulting in decreased risk of infection. However, the confinement method, such as clamps, as used in conjunction with the invention, prevents a significant amount of antimicrobial agent from leaking into the bloodstream on a regular basis.

In addition, separation between the antimicrobial agent and blood can result in lower infection rate, fewer side effects, and less risk of developing resistant bacteria because a non-antibiotic antimicrobial is used. In certain embodiments, the present invention creates a physical barrier between the blood and the antimicrobial agent. The barrier greatly reduces the exchange of antimicrobial agent with blood circulating in the body, resulting in fewer side effects from the antimicrobial agent. This can result in a more consistent level of antimicrobial agent along the length of the catheter adjacent to the cap. Additionally, the barrier reduces the amount of antimicrobial agent entering the bloodstream, thus reducing the risk of an adverse reaction to the agent or developing organisms resistant to the antimicrobial agent. In comparison, it is well-known that liquid locking agents can and do routinely migrate into the bloodstream, and the blood can migrate into the catheter, thus reducing the effectiveness of the antimicrobial agent, increasing the possibility of bacteria entering the bloodstream and increasing the rate of thrombosis in the catheter. The act of flushing the catheter lumen with a fluid agent into the lumen will result in the removal of blood from the lumen and thus reduce the risk of thrombosis. If the liquid agent is an anti-thrombotic lock, such as heparinized saline or saline with 4% sodium citrate, the risk of thrombosis is further reduced. The use of a confinement means, as described in the present invention as a swellable elongate member tip, swellable elongate member, or catheter clamp, prevents the blood from reentering the lumen and results in a lower risk of thrombosis in the lumen.

A further aspect of the invention relates to protecting the caps from contamination prior to use and during handling in order to keep the elongate member and luer sterile prior to insertion into the catheter. A shield over the elongate member and luer may be used. A standard shield, which protects one luer and elongate member, is suitable for keeping one elongate member and luer sterile. A novel shield is hereafter described which improves handling while maintaining sterility protection, and facilitates low-cost injection molding. The novel shield holds two caps within one shield body, where the two caps are held 180 degrees opposed in an axially offset manner with at least a portion of the two elongate members axially overlapping one another, with a physical barrier between the two caps. The shield may have threads to provide a means for removably attaching the caps to the shield. This novel configuration allows the user to hold one piece rather than two, thus casing handling and decreasing the risk of dropping the caps. The barrier between the two caps ensures that, when one cap is removed from the shield, that the other cap remains sterile. The caps, secured within the shield, may be packaged in a pouch using a suitable packaging material, such as a metal film with a polymer laminate to facilitate heat sealing. The metal layer is useful to minimize adverse effects of humidity. The device, inside the pouch, may be sterilized using gamma radiation or other suitable sterilization method. Gamma radiation has the advantage of effectively sterilizing the product while it is contained within moisture-proof packaging.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

Research and development into preventing catheter-related bloodstream infections (CRBSI) over the last twenty years has been focused on methods for killing the bacteria along the inside and outside length of the catheter. This research has resulted in success at reducing the incidence of CRBSI in some catheter types. For instance, commercially successful antimicrobial coated catheters have resulted in a decrease in the incidence of infection in applications that use short-term (non-tunneled) catheters. However, these coating wash off with use and therefore are not effective for long-term applications. The use of long-term (tunneled, cuffed) hemodialysis catheters result in approximately 2.3 bloodstream infections every 1000 catheter days. Said another way, a patient dialyzing with a hemodialysis catheter can expect to develop a bloodstream infection, on average, every 14 months. To fix this remaining problem, much of today's research is focusing on ways to eliminate biofilm within catheters and on ways to produce longer lasting antimicrobial coatings that are capable of killing organisms within catheters.

Infectious organisms typically colonize a catheter in three distinct ways. First, the infectious organisms may colonize the catheter by traveling in the bloodstream and eventually adhering to the catheter. This form of transmission is believed to be rare. Second, the infectious organisms may colonize the catheter by traveling along the outer wall of the catheter after entering at the catheter's body exit site. This method of infection transmission has been greatly reduced by tunneling the catheter under the skin for several centimeters, and by the addition of a cuff on the outer wall of the catheter. Body tissue grows into the cuff and creates a barrier for infection. Third, the infectious organisms may colonize the inner lumen of the catheter, entering at the hub and/or adaptor of the catheter connector, eventually migrating down the lumen of the catheter to the bloodstream. This method of infection transmission is a leading cause of bloodstream infections in patients with long-term indwelling catheters. Therefore, a need exists for improved devices, systems, and methods for eliminating, treating, and preventing such contamination.

The present invention prevents, reduces and can even eliminate infectious organisms from the entry region of a catheter or tube, and from within the inner luminal surface of a catheter or other similar medical devices by providing a means for the prolonged presence of an antimicrobial agent and/or providing a means for periodically scrubbing the entry region and/or lumen of the catheter or other medical device to remove the infectious organisms and the biofilm in which infectious organisms proliferate.

The present invention includes methods and devices for killing organisms and preventing organism proliferation and biofilm formation in catheters so that organisms aren't able to exit the catheter and enter the bloodstream of a patient. The article of the present invention prevents, or reduces the number of, organisms reaching the bloodstream by employing any or all of the following three prevention methods: 1) physically blocking migration of organism outside the catheter, 2) killing organisms along the threads, end face and luer connector (inside and outside of the connector) at the proximal end (outside of the body) of the catheter using an antimicrobial, and/or 3) killing organisms within a confined region of the catheter using an antimicrobial agent and/or a physical barrier in the catheter lumen. A fourth mode of action, scrubbing the catheter wall (to physically remove organisms adhered to the interior wall section upon removing the cap from the catheter) may also be used in conjunction with the other methods and devices.

As noted above, the invention is directed in part to an antimicrobial agent inside the catheter. The antimicrobial agent can be delivered as a coating that elutes from a coated elongate member, that is coated on, or impregnated into, an elongate member (such as 250 μg of chlorhexidine acetate in a layer approximately 2 μm thick along a 17 mm long×1.9 mm diameter elongate member/rod). The elongate member has the added benefit of displacing fluid from within the catheter as it is inserted, transferring the solution to the outer proximal region of the catheter connector (end face and treads). Antimicrobial agent from the cap dissolves into the displaced fluid, and thereby disinfecting the proximal end of the connector. Furthermore, when the fluid dries, it deposits a coating of chlorhexidine acetate or other appropriate antimicrobial on the connector as described above. As an alternative to using the elongate member, chlorhexidine acetate or other antimicrobial agent may be delivered by a coating on a luer tip (such as 250 μg of chlorhexidine acetate in a layer that is approximately 20 μm thick). The luer portion is also coated with an antimicrobial agent (such as 50 μg of chlorhexidine acetate in a layer that is approximately 0.4 μm thick). It is also possible to inject an antimicrobial agent into the catheter using a syringe, or to deliver antimicrobial agents by way of the connector tip cavity (dry dissolvable amount, applicable for Citrate or others requiring large amounts of antimicrobial agent).

Figure 1A:
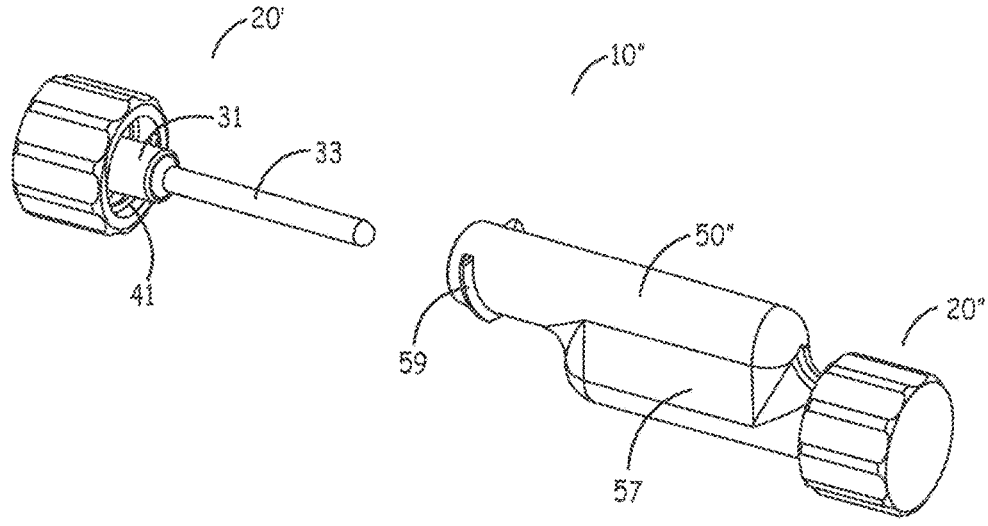
FIG. 1A is a perspective view of a dual-shield with two caps made in accordance with the preferred implementation of the invention. One cap is inserted into the dual shield; the other cap is not inserted.

Referring now to the figures, example implementations of the invention are shown. FIG. 1A shows an exploded view of a dual shield system 10" that includes an arterial cap 20', a venous cap 20" and a shield 50"; the colors are typically chosen to match the standard colors used in hemodialysis: red for the arterial cap 20' and blue for the venous cap 20". The dual shield system 10" contains two caps within the same shield 50". The shield 50" provides for easier handling because there are fewer parts to handle and hold. The dual shield system 10" is packaged within a heat-sealed foil-pouch (not shown) and gamma sterilized. The foil-pouch is opened at the clinic immediately before use of the caps. The cap threads 41 removably engage the dual shield threads 59 to allow easy removal of the caps 20', 20" from the shield 50". The flattened side 57 creates a convenient means for gripping the shield as the caps 20', 20" are removed. In addition, the flattened side 57 disrupts the rotational symmetry of the shield 50", thus making the shield system 10" resistant to rolling onto the floor or being dropped.

Figure 1B:
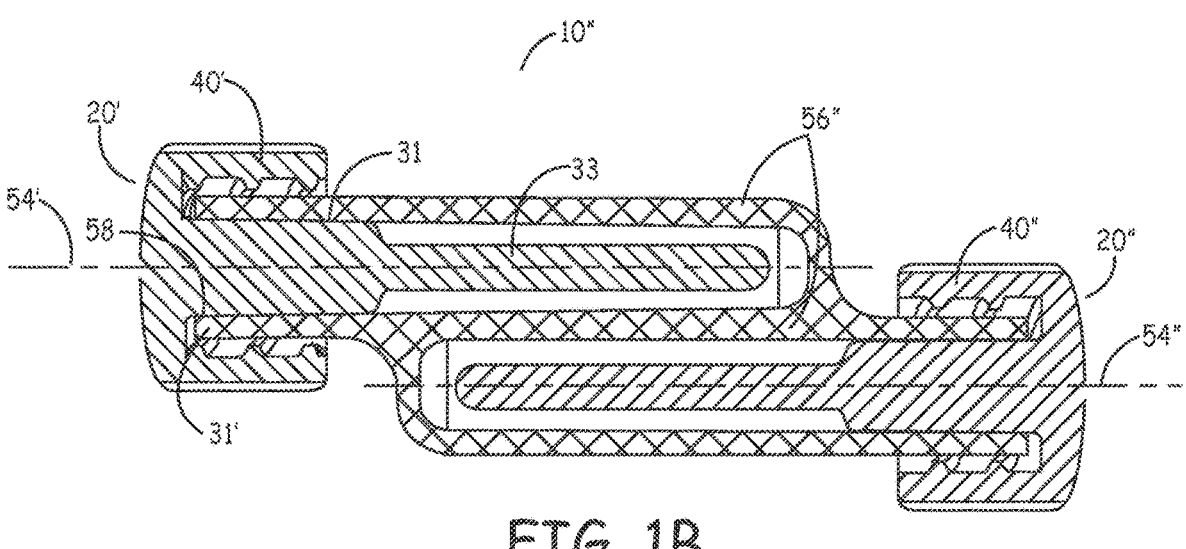
FIG. 1B is a side cross section view of two caps inserted into a dual-shield and is made in accordance with the preferred implementation of the invention.

FIG. 1B shows a cross section of a dual shield system 10" with an arterial cap 20' and a venous cap 20" each inserted into a shield 50". The shield 50" is designed to keep the caps 20', 20" axially offset as shown by the arterial cap axis 54' and the venous cap axis 54". The offset axis is advantageous over a coaxial design because it decreases the length of the system 10", allowing it to fit into a shorter pouch and making it easier to handle. In addition, the caps 20', 20" are 180 degrees opposed from each other, thus making the retaining rings 40', 40" physically separated from one another. This is makes the retaining rings 40', 40" easier to grasp because the arterial retaining ring 40' does not physically block finger access to the venous retaining ring 40", and vice versa. The shield 50" provides protection to the caps 20', 20" and further aids maintenance of sterility prior to use because each of the caps 20', 20" are separated by a wall 56". In an example embodiment, the most proximal portion 31' of the male luer 31 contacts the receiving edge 58 of the dual shield 50". The rest of the male lure 31 does not contact the wall 56", and thereby minimizes the risk of removing the antimicrobial coating on the male luer 31. Typically the elongate member 33 also does not contact the wall 56" so as to minimize the risk of removing the antimicrobial coating.

Figure 2A:
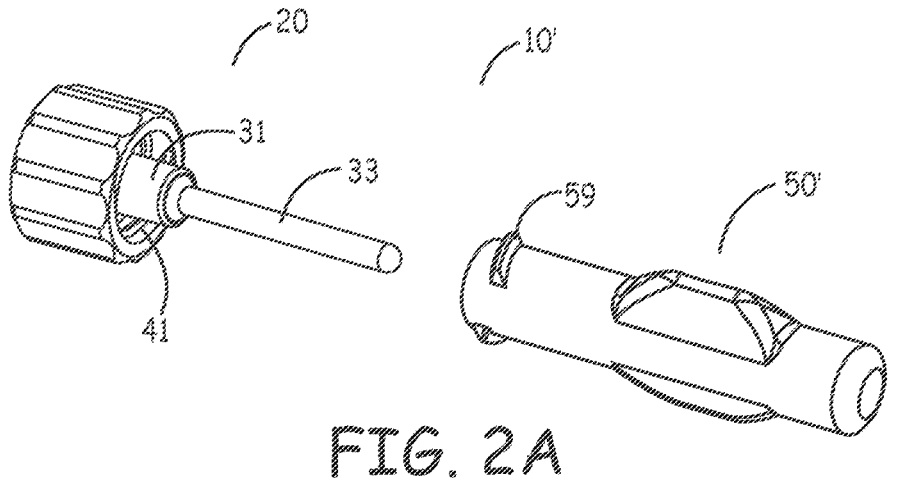
FIG. 2A is a perspective view of an elongate member and mono shield made in accordance with an implementation of the invention. The cap is shown not inserted into the mono shield.

FIG. 2A shows a perspective view of a mono shield system 10' with a cap 20, and a shield 50'. The shield 50' contains one cap within the housing. The mono shield system 10' is packaged within a heat-sealed foil-pouch (not shown) and gamma sterilized. The foil-pouch is opened at the clinic immediately before use of the cap. The cap threads 41 removably engage the mono shield threads 59 to allow easy removal of the cap 20 from the mono shield 50'.

Figure 2B:
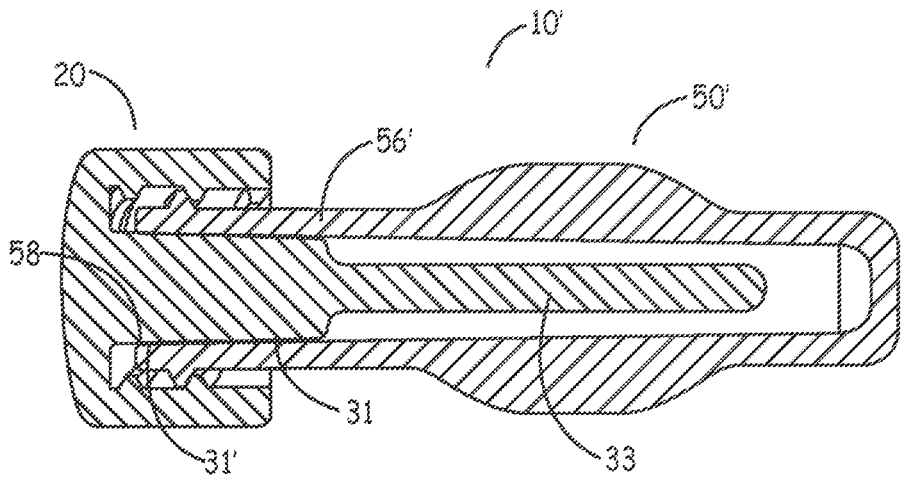
FIG. 2B is a side cross section view of a cap inserted into a mono shield made in accordance with an implementation of the invention.

FIG. 2B shows a cross sectional view of a mono shield system 10' with a cap 20 inserted into a mono shield 50'. The mono shield 50' provides protection to the cap 20 and further ensures that sterility is maintained prior to use. This is accomplished by enclosing the cap 20 by a wall 56". In an example embodiment, the most proximal portion 31' of the male luer 31 contacts the receiving edge 58 of the mono shield 50'. The rest of the male lure 31 does not contact the wall 56', and thereby minimizes the risk of removing the antimicrobial coating on the male luer 31. The elongate member 33 also preferably does not contact the wall 56' in order to minimize the risk of removing the antimicrobial coating.

Figure 3A:
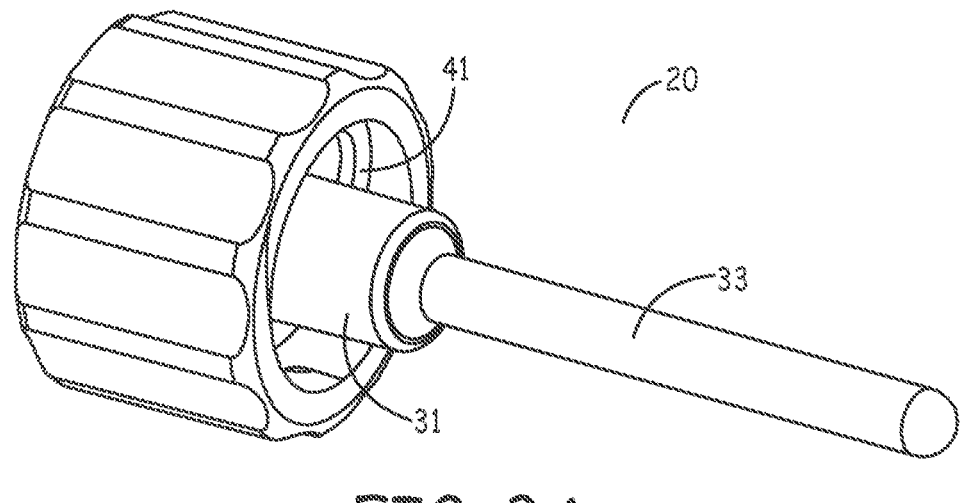
FIG. 3A is a perspective view, looking from the distal end of a cap, made in accordance with the preferred implementation of the invention.

FIG. 3A shows a cap 20 made in accordance with an example implementation of the invention. The cap 20 can be injected molded as a single unit out of a thermoplastic polymer resin to allow high volume production at low manufacturing costs. Suitable polymer will produce a durable part such that the elongate member 33 may be bent without breaking. Polymers with a minimum elongation at break of 100% are preferred. In addition, the polymer will typically allow a solvent (which is used in the antimicrobial coating process) to wet the surface evenly until the solvent evaporates, and the antimicrobial agent should adhere well to the surface such that the coating does not flake or fall off during handling. Various polymer materials may be used that meet these requirements, such as polyester, nylon, polyetherimide, polypropylene, polyvinyl chloride or other similar materials. Alternatively, the elongate member 33 may be manufactured using a dissolvable material which is impregnated with an antimicrobial agent, thus the antimicrobial is released into the solution when the elongate member 33 dissolves.

Portions of the cap 20 are typically coated and/or impregnated with an antimicrobial agent. In one embodiment, the antimicrobial agent is applied as a coating, with different amounts optionally applied to the elongate member 33, the male luer 31, and the cap threads 41. The antimicrobial agent can also be incorporated within the bulk polymer material, but coating the surface is preferred because surface coatings can generally be released into solution more rapidly than bulk agents; additionally surface coatings tend to require less overall antimicrobial agent than bulk agents because the antimicrobial agent on the surface is more readily dissolved. In some implementations a combination of surface coatings and incorporation into bulk polymer materials is used.

Suitable methods of coating the cap 20 are spraying and dipping, with spray coating being desirable because the amount of antimicrobial agent applied to each region (elongate member 33, male luer 33, and cap threads 41) can more easily be adjusted without affecting the amount located on other regions.

Figure 3B:
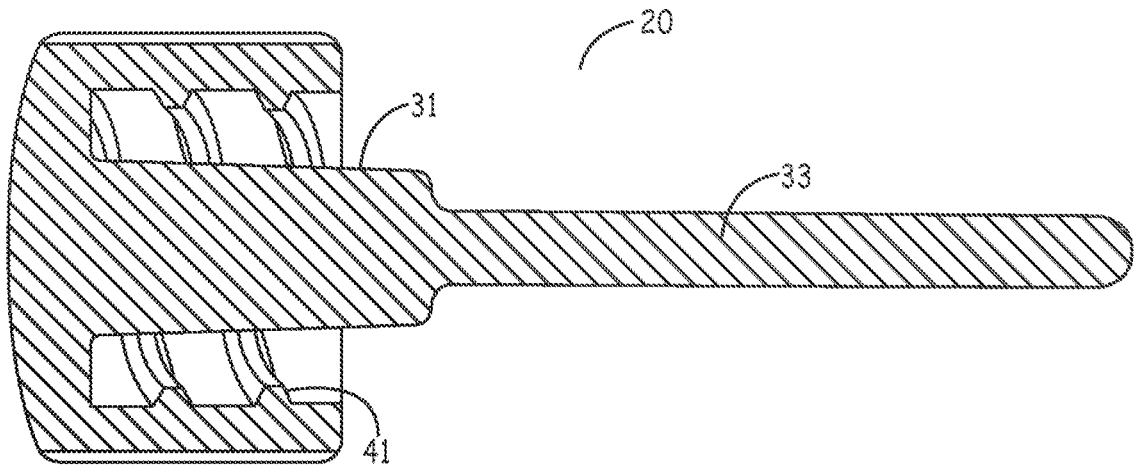
FIG. 3B is a side cross section view of a cap made in accordance with the preferred implementation of the invention.

FIG. 3B shows a cross section of a cap 20 made in accordance with an embodiment of the invention. The length and diameter of the elongate member 33 is sized to fit into a medical device. In the embodiment described herein, the catheter is a hemodialysis catheter. The male lure 31 and the cap threads 41 can be manufactured in accordance with the International Organization for Standardization standard ISO 594-2:1998 (E) to be compatible with all hemodialysis catheters which are made according to the standard.

Figure 4A:
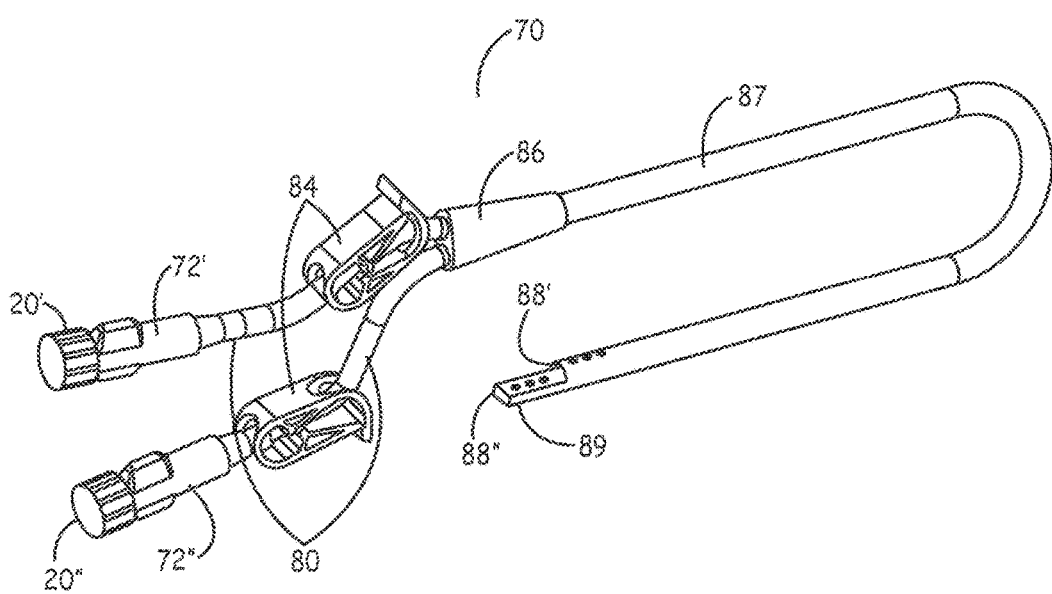
FIG. 4A is a perspective view of two caps made in accordance with the preferred implementation of the invention, and a catheter. The caps are shown inserted into the catheter.

FIG. 4A depicts a hemodialysis catheter 70 for use in conjunction with an embodiment of invention, and is shown with an arterial cap 20' in the arterial hub 72', and a venous cap 20" in the venous hub 72". When used with a hemodialysis patient, the two-lumen tube 87 is partially tunneled below the patient's skin, from the upper chest to the jugular vein. The two-lumen tube 72" enters the jugular vein and continues until the catheter tip 89 is in the region of the right atrium of the heart. The arterial lumen 88' runs inside the catheter 70 from the arterial hub 72' until exiting at the catheter tip 89. The venous lumen 88", similarly, runs inside the catheter 70 until it exits near the catheter tip 89. If bacteria or fungus are in either or both lumens 88', 88", these infection-causing organisms may enter the bloodstream and result in a systemic bloodstream infection, and therefore prevention of the entry and growth of microorganisms into the catheter 70 is important. The catheter contains a junction 86, where the extension tubes 80 transition from two tubes with two lumens into one tube with two lumens; the two lumens 88', 88" run the entire length of the catheter 70, from hub 72', 72" to catheter tip 89 without fluidly connecting with the other lumen. The arterial hub 72' is attached to the proximal end of one extension tube 80, and the venous hub 72" is attached to the proximal end of the other extension tube 80. In the depicted embodiment, a clamp 84 is positioned on each of the extension tubes 80, allowing the flow in the lumen to be blocked or opened. In practice, the clamps 84 are closed except during a dialysis session or other transferring of fluids within the catheter 70. The clamps 84 are typically repositioned each time the clamps 84 are opened in order to minimize the risk of damaging the extension tube 80 through multiple clamping in the same location.

Figure 4B:
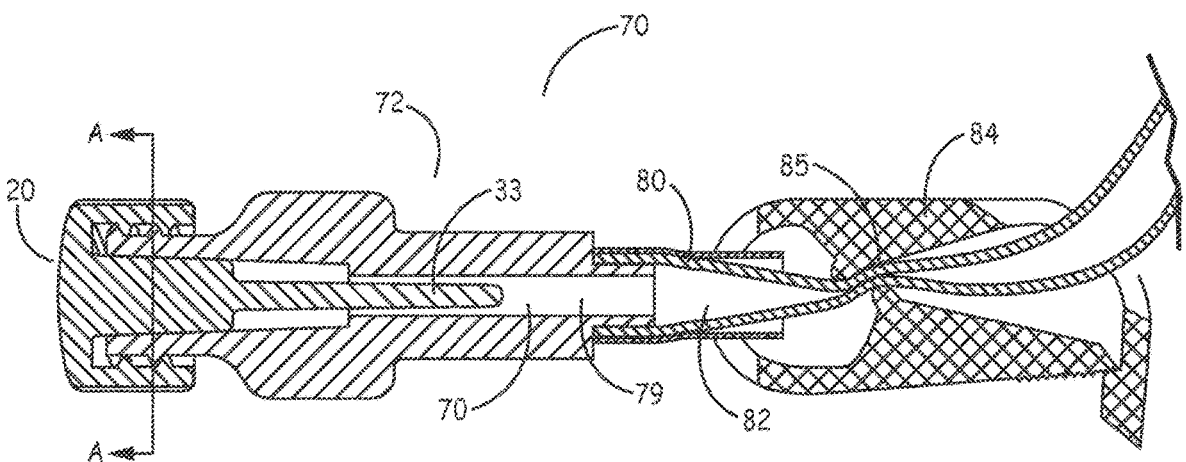
FIG. 4B is a side cross section view of a cap made in accordance with the preferred implementation of the invention, and inserted into a catheter.

In reference to FIG. 4B, the clamp 84 is shown located in close proximity to the hub 72. The clamp 84, when closed, creates a pinch point 85 which blocks the fluid flow in the lumen. Preferably the elongate member 33 will be short enough to ensure that the clamp 84 does not clamp onto the elongate member. In addition, the elongate member 33 must possess a small enough diameter to ensure that it can physically fit within the hub lumen 79. In embodiments where the elongate member 33 is long enough to enter the extension tube 80, the diameter of the extension tube must also fit within the extension tube lumen 82. The elongate member 33 should preferably be stiff enough to allow for insertion into the hub 72 without requiring sheaths, tubes or other insertion aids.

The surface area of the elongate member 33 should be large enough to allow for the desired amount of antimicrobial agent to be coated on the surface using spraying or dipping operations (or other application methods, including incorporation directly into the elongate member). The surface area is generally sized to produce an acceptable dissolution rate such that the antimicrobial agent enters the lock solution 90 at an acceptable rate and dosage. It is desirable for the antimicrobial agent to reach an effective level within an hour of the cap 20 being inserted into the catheter 70.

If the elongate member extends into the pinch point 85 of the clamp 84, it can potentially cause damage or leaking of the lock solution 90. Therefore the length of the elongate member 33 should be sufficiently short to ensure that it does not reach the pinch point 85 of the clamp 84. Suitable diameters for the elongate member 33 include 1.0 mm to 2.0 mm; and 1.7 mm to 1.9 mm. A suitable length includes less than 20 mm for the elongate member 33, alternatively less than 30 mm, less than 40 mm, or less than 10 mm. A particularly desirable length is 17 mm to 19 mm, but can vary for use with various catheters.

Figure 4C:
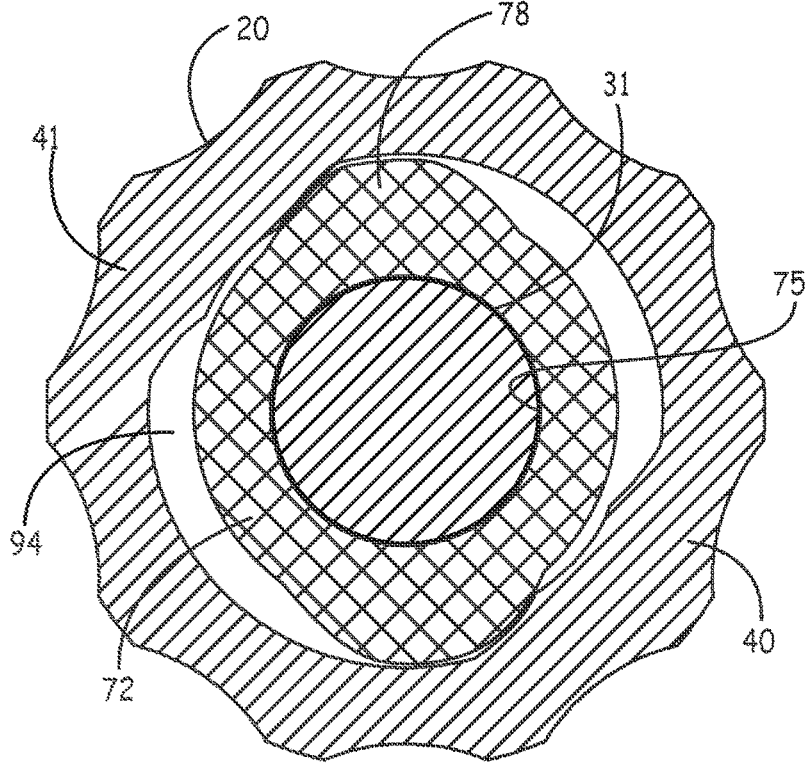
FIG. 4C is an end cross section view of a cap made in accordance with the preferred implementation of the invention, and inserted into a catheter.

In reference to FIG. 4C, an embodiment is depicted showing the end section view A-A as indicated in FIG. 4B, the cap 20 is shown fully inserted into the catheter hub 72. When fully inserted, the male luer 31 contacts the female luer 75 to create a fluid tight seal. The cap threads 41 engage the catheter threads 78 to retain the cap 20 on the hub 72. However, after the cap 20 is fully inserted into the hub 72, a void 94 is present between the retaining ring 40 and the hub 72. This void 94 can be a pathway for pathogenic organisms to travel along, thus allowing contamination of the hub surfaces with pathogenic organisms in the region between the retaining ring 40 and the hub 72. In order to reduce the incidence of catheter-related bloodstream infections, it is desirable to reduce or eliminate the number of pathogenic organisms in this region.

Figure 5A:
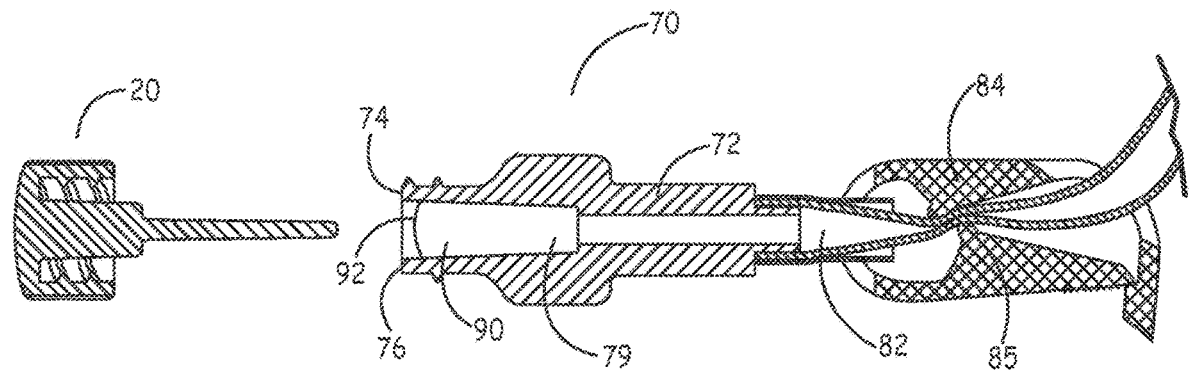
FIG. 5A is a side cross section view of a cap made in accordance with the preferred implementation of the invention, prior to cap being inserted into a catheter.
Figure 5B:
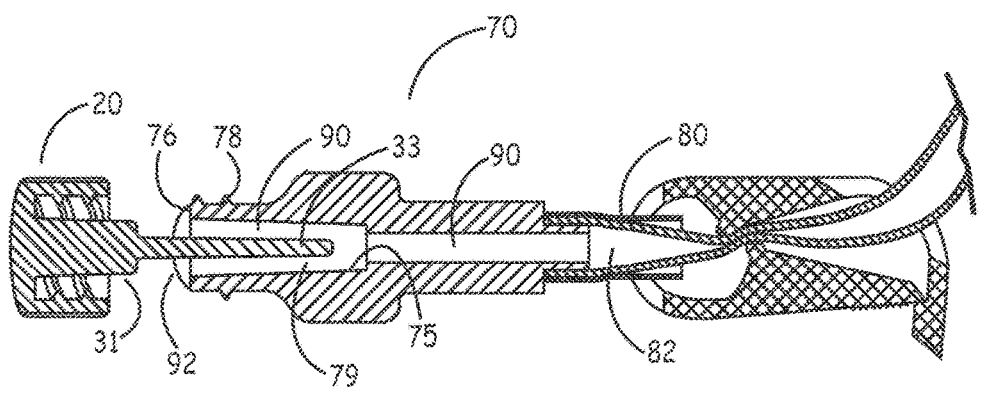
FIG. 5B is a side cross section view of a cap made in accordance with a preferred implementation of the invention, as the cap is being inserted into a catheter.
Figure 5C:
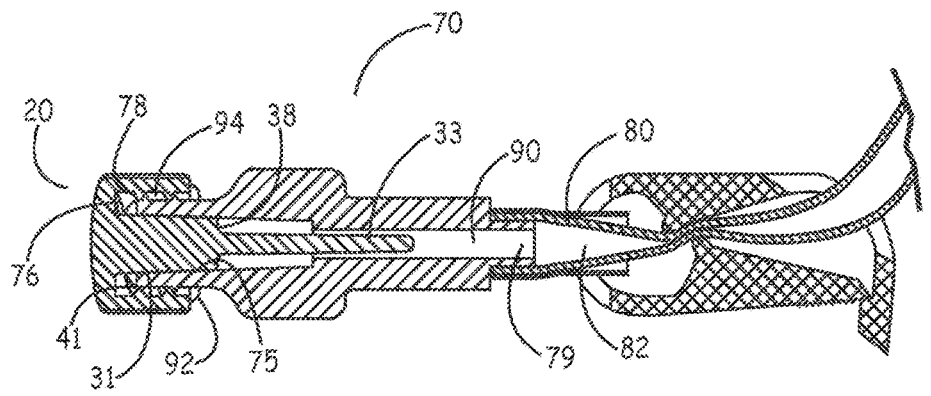
FIG. 5C is a side cross section view of a cap made in accordance with a preferred implementation of the invention, with the cap fully inserted into a catheter.

Referring now to FIGS. 5A to 5C, various stages of installation of cap 20 are shown, wherein the insertion of the cap (with an elongate member) results in the flow of an anti-microbial containing liquid out the end of the catheter hub to kill microorganisms that would otherwise potentially intrude into the hub and then the catheter lumen. In FIG. 5A, the cap 20 is shown immediately prior to being inserted into the hub 72 of a catheter 70. Within the hub lumen 79 is a liquid locking solution 90, the most proximal portion of which forms a meniscus 92. The locking solution for hemodialysis catheters is most often heparinized saline (100 IU/ml to 5000 IU/ml of heparin), sodium citrate solution (typically 4% sodium citrate), or saline. Patient care technicians and nurses are trained to keep the meniscus 92 at the proximal end 74 of the hub 72. However, it is not unusual for the meniscus to fall several millimeters within the hub lumen 79. The antimicrobial agent must produce the desired effect in any of the standard lock solutions. In practice, the clamp 84 remains closed (producing a pinch point 85) unless fluids are being transferred through the catheter 70; this is standard practice because it decreases the risk of introducing an air embolus into the patient's bloodstream through catheter 70.

In reference to FIG. 5B, the elongate member 33 is shown partially inserted into the hub lumen 79. The elongate member 33 displaces lock solution 90, which results in the meniscus 92 being pushed out of the lumen 90 and onto the end face 76 of the hub 70. Eventually, as the cap 20 continues to be inserted, the meniscus 92 (and lock solution 79) will travel over the catheter threads 78.

Next, referring to FIG. 5C, the cap 20 is shown fully inserted into the catheter 70. In this embodiment, the meniscus 92 travels beyond the void 94, completely filling the void 94 with lock solution. The lock solution causes the antimicrobial agent to dissolve, resulting in a transfer of antimicrobial agent from one or more of the coated parts (the elongate member 33, the male luer 31, and cap threads 41) into the solution. In addition, insertion of the elongate member into the locking solution further causes a transfer of antimicrobial agent to the previously uncoated parts such as the wall defining the inner hub lumen 79 and extension lumen 82, the female luer 75, the end face 76, and the catheter threads 78. Within several hours the solution within the void 94 may dry. In this manner an antimicrobial coating becomes transferred to the catheter threads 78 and the end face 76, resulting in an enhanced ability to kill any organisms on the catheter threads 78 and the end face 76, even if the organisms contaminate the surfaces after the solution dries. In practice, the void is often times infiltrated with sweat that contains organisms. In this scenario the dried antimicrobial agent becomes hydrated by the sweat, killing organisms that may be present in the sweat. Furthermore, the catheter threads 78 and the end face 76 become replenished with antimicrobial agent every time a new cap 20 is inserted. In current practice, a new cap is used after every dialysis session. The ability of the cap 20 to replenish the antimicrobial agent on a catheter 70, into a targeted location with a high risk of serving as a microorganism source, overcomes a significant shortcoming of antimicrobial coated catheters in which the antimicrobial agent wears off with use or is only applied to the interior of the catheter. A desirable amount of antimicrobial agent on the catheter threads 78 is 20 µg to 2 mg, alternatively 200 µg to 1.5 mg, and desirably 500 µg to 1.2 mg of chlorhexidine acetate. However, it will be understood that different levels can also be achieved with success.

The male luer 31 makes contact with the female luer 75 to create a fluid tight seal. These parts are typically manufactured in accordance with the International Organization for Standardization standard ISO 594-2:1998 (E) in order to ensure proper sealing and intermateability. However, the junction between the male luer 31 and the female luer 75 is not fluid tight along the entire length of the interface. Some manufacturers of medical device hubs intentionally manufacture their female luers such that the male luer contacts the female luer near the male luer end face. This is done in order to reduce the risk of the splitting the hub. However, the unintended consequence is that proximal end of the luer interface allows for the potential infiltration of organisms. Once the organisms are present, they may be pushed further into hub lumen 79 by current caps (or other devices) the next time a cap (or other device) is inserted. Once the organisms are within the hub lumen (distal to the male luer) they can multiply, resulting in planktonic and sessile organisms, and eventually a biofilm. This problem can be countered by placing an antimicrobial agent along the male luer 31. The antimicrobial agent kills organisms that may be or become present along the female luer 75 before the organisms have a chance to be pushed into the hub lumen 79 or further multiply. Even with these protective measures, there is still a possibility that some organisms can make it beyond the female luer 75. To overcome that potential shortcoming, the preferred embodiment also contains antimicrobial on the elongate member 33, which dissolves or elutes into the lock solution 90, to kill organisms in the hub lumen.

The minimum amount of antimicrobial agent on elongate member 33 was determined through laboratory testing in which elongate members were placed into catheters under a variety of lock solutions and challenge organisms. The type of lock solution was varied among saline, heparinized-saline, 4% sodium citrate solution, and human serum. A variety of challenge organisms were used, such as *Candida albicans, Pseudomonas aeruginosa, Staphylococcus aureus*, and *Escherichia coli*. Testing performed by the inventors showed a dose response; the more chlorhexidine acetate contained on the elongate member 33, the more organisms that are killed in the catheter 70.

The maximum amount of antimicrobial agent that is placed on each of the cap's surfaces was developed by first reviewing how much antimicrobial is safe for the patient and then comparing that to how much antimicrobial agent the patient can potentially be exposed to by each of the cap's 20 surfaces that contain antimicrobial agent (elongate member 33, male luer 31, and cap threads 41). The amount of antimicrobial that is safe for the patient was determined by reviewing published information on levels (especially bloodstream levels) that are generally regarded as safe for patients.

Testing was conducted in order to derive how much antimicrobial agent the patient can potentially be exposed to from cap 20. The testing was designed to determine the transfer efficiency of antimicrobial agent from each applicable component (elongate member 33, male luer 31, and cap threads 41) to the bloodstream. In order to determine the potential bloodstream level, consideration was given for potential patient exposure that could occur under a variety of conditions, including unusual use or misuse (such as injecting the lock solution into the patient's bloodstream instead of aspirating the solution). The potential patient exposure was determined for each component individually and for the entire cap 20.

The minimum amount of antimicrobial agent on the elongate member 33 is the amount required to obtain an acceptable reduction (also referred to as kill) of infection causing organisms. The volume of solution that the antimicrobial agent dissolves into is important to understand because the more solution that is present, the more dilute the antimicrobial agent can become. The confined volume of lock solution 90 within the lumen is defined by the location of the meniscus 92, the geometry of the hub lumen 79, the geometry of the extension lumen 82, and the location of the pinch point 85. Since each of these items may vary, there is a considerable range of confined fluid volumes that is possible. After accounting for the design variations of existing hemodialysis catheters, it is evident that the preferred embodiment needs to produce a therapeutic concentration of antimicrobial agent within a 0.7 ml volume. In one embodiment, the amount of chlorhexidine acetate on the elongate member 33 is greater is 10 µg to 5 mg. In an alternative embodiment, the amount of chlorhexidine acetate is 100 µg to 2 gm. In yet another embodiment, the elongate member contains 250 µg to 550 µg.

These embodiments can produce broad spectrum kill of the target organisms, yet result in a low enough dose of chlorhexidine acetate that, even if all of the lock solution containing chlorhexidine acetate is injected directly into the bloodstream, it will result in a bloodstream level that remains at safe levels.

Figure 6:
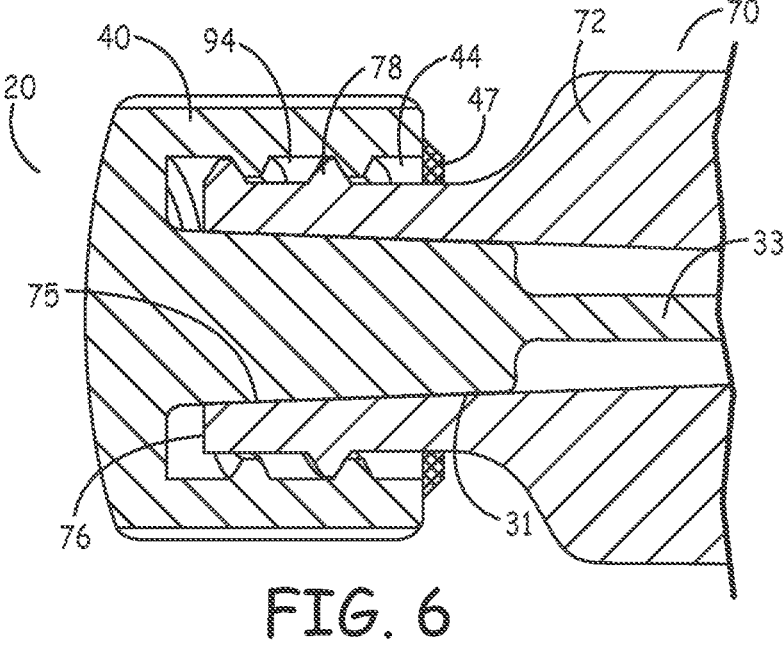
FIG. 6 is a side cross-section view of a cap with a seal at the distal end of the retaining ring made in accordance with an implementation of the invention, inserted into a catheter.

In reference to FIG. 6, a cap 20 is shown fully inserted into a catheter 70. This embodiment contains an end seal 47. The end seal 47 provides additional benefit by preventing organisms from entering the distal opening 44 thereby preventing the organisms from subsequently progressing through the void 94 where they could then contaminate the end face 76 and female luer 75. Reducing the number of organisms that can enter distal opening 44 can further reduce the incidence of CRBSI. The end seal 47 can be made of an elastic material so it is capable of stretching over the catheter threads 78 while the cap 20 is being inserted, and it should also conform to the shape of the hub 72 so it creates an effective organism-blocking seal. The end seal 47 is preferably made of a durable material so it does not rip or tear. It should be thin and flexible enough so it is easy to insert. The end seal 44 allows fluid to escape as the cap 20 is being inserted onto the catheter 70, yet acts as a barrier to substantially retain the lock solution that was pushed into the void 94 during insertion. In the preferred embodiment, this is accomplished by keeping the wall thin and flexible enough to allow the increased pressure to escape where the end seal 47 contacts the hub 72. In an example embodiment, the end seal 47 is over molded onto the retaining ring 40. A thermoplastic elastomer, such as Exxon Mobile's Santoprene, can be used. However, other materials, such as silicone, may be suitable. In an embodiment, the end seal 47 is in the range of 0.005 inch to 0.100 inch thick. In another embodiment, the end seal 47 is in the range of 0.010 inches to 0.040 inches thick.

The lock solution in void 94 also acts as a barrier to organism infiltration. It contains antimicrobial agent that has dissolved from the cap 20 surfaces (elongate member 33, male luer 31, and catheter threads 78). In a desired embodiment, the antimicrobial levels result in an antimicrobial concentration that is highly effectively at killing a broad spectrum of organisms.

Figure 7:
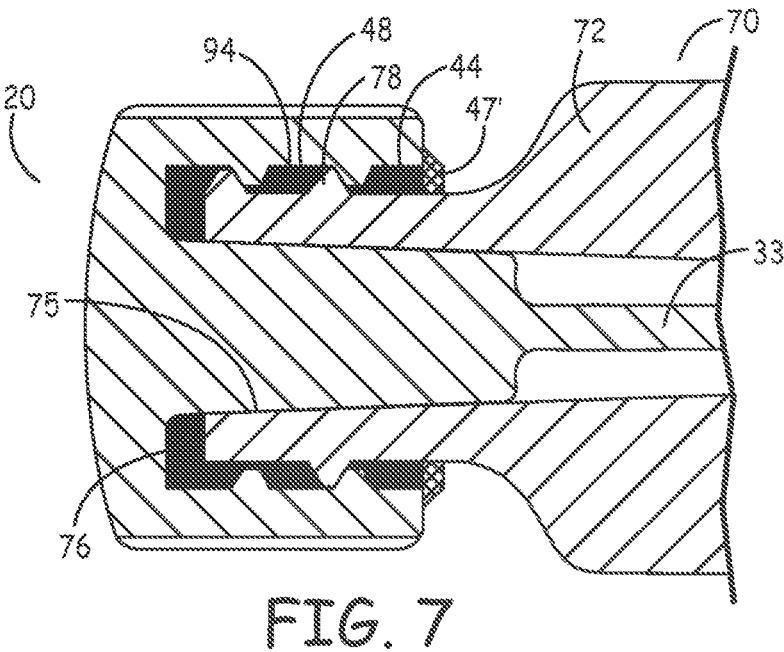
FIG. 7 is a side cross-section view of a cap with foam along the threads of the retaining ring made in accordance with an implementation of the invention, and inserted into a catheter.

In reference to FIG. 7, the cap 20 is shown fully in cross section inserted into a catheter 70. This embodiment can contain a thread seal 48 that is impregnated with an antimicrobial agent in the same amount as (and in place of) the amount on the cap threads 41 of FIG. 5C. The thread seal 48 provides additional benefit by preventing organisms from entering the distal opening 44 and, since the void 94 is now occupied with the thread seal 48, it prevents organisms from progressing through the occupied void 94 where they would otherwise contaminate the end face 76 and female luer 75. Reducing the number of organism that can enter distal opening 44 can further reduce the incidence of CRBSI. The thread seal 47' is preferably made of an elastic foam material that is capable of conforming around the catheter threads 78 while the cap 20 is being inserted, and it should also conform to the shape of the hub 72 so it creates an effective organism-blocking seal. The most distal end of the thread seal 47' often has a thin layer of closed polyurethane to help reduce evaporation of the solution. The thread seal 48 is desirably made of a durable material so it does not rip or tear. One aspect of the thread seal 48 is that it allows fluid to escape as the cap 20 is being inserted into the catheter 70, yet it acts as a barrier to substantially retain the lock solution that was pushed into the filled void 94 during insertion. In the preferred embodiment, this is accomplished by manufacturing the thread seal 48 out of an open cell hydrophilic medical polyurethane foam and having a thin layer of solid polyurethane at the most distal end of the thread seal 47'. The distal end of the thread seal 47' is desirably thin, such as 0.001 to 0.020 inch, and flexible enough to allow the increased pressure to escape where it contacts the hub 72. The thread seal 48 and the antimicrobial agent incorporated therein also acts as a barrier to organism infiltration. It contains antimicrobial agent that has dissolved from the cap 20 surfaces (such as one or more of the elongate member 33, male luer 31, and thread shield 48).

Figure 8A:
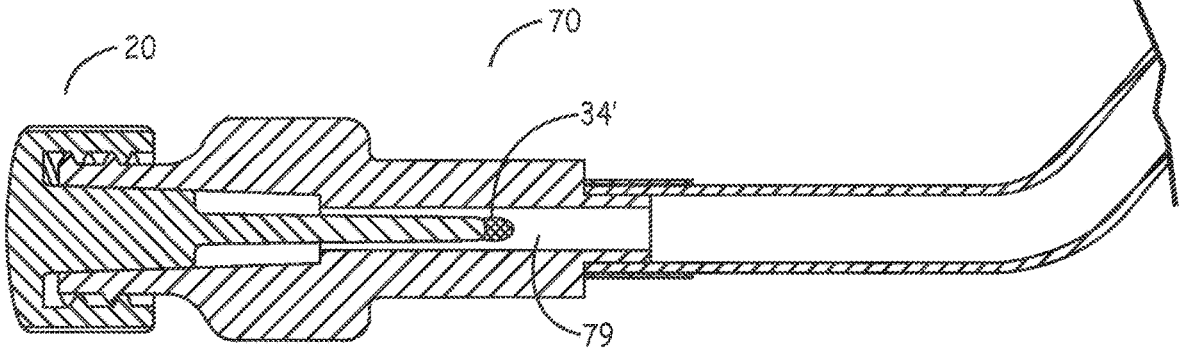
FIG. 8A is a side cross-section view of a cap with a swellable tip made in accordance with an implementation of the invention, inserted into a catheter. The tip is shown in its unswollen state.

FIG. 8A refers to an alternative embodiment of the cap 20 which possesses a novel tip 34' that has a diameter that is smaller than the diameter of the hub lumen 79 when the tip 34' is inserted into a catheter 70, but subsequently expands in size. This embodiment is especially beneficial when the cap 20 is used in a catheter 70 that does not have a clamp for confining the solution, or in cases where it is desirable to further limit the amount of antimicrobial agent required (less is required because the volume of confined solution is lower). The tip 34' is shown in FIG. 8A in its unswollen state during insertion in order to allow the elongate member to be easily inserted and to minimize its potential for pushing organisms distal to the tip 34' by a plowing action. The elongate member in a preferred embodiment remains sufficiently stiff while it is being inserted onto into the catheter 70 and it does not require any extra parts or aids for insertion.

Figure 8B:
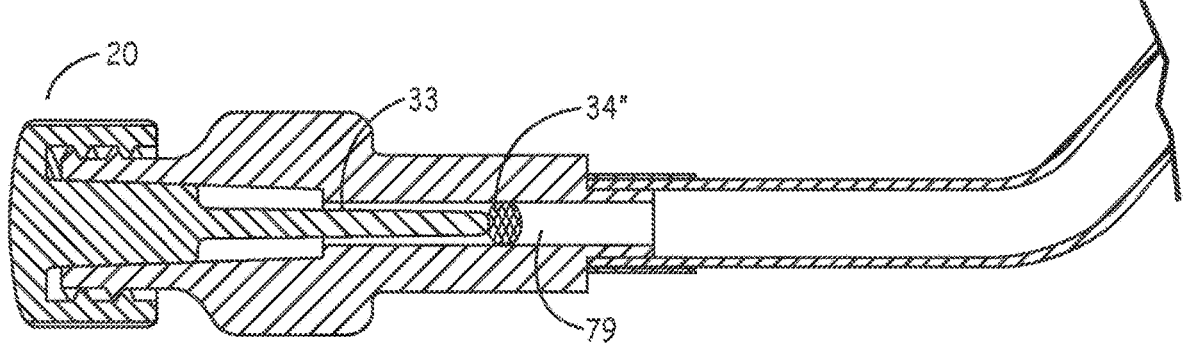
FIG. 8B is a side cross-section view of a cap with a swellable tip made in accordance with an implementation of the invention, inserted into a catheter. The tip is shown in its swollen state.

FIG. 8B refers to an alternative embodiment of the cap 20 as described in reference to FIG. 8A, except the tip 34" is shown in its swollen state. In the depicted embodiment the diameter of the tip 34" is equal to the diameter of the hub lumen 79 in its swollen state; the tip 34" preferably conforms to the surface of the hub lumen 79 as it swells. The swollen tip 34" is beneficial for confining the solution, or in cases where it is desirable to further limit the amount of antimicrobial agent required (less is required because the volume of confined solution is lower). The tip 34" is removable from the hub lumen 79 when reasonable removal force is applied to the cap 20. This is achieved by choosing the material and size the tip 34" such that, when it is in its swollen state, the normal force that the tip 34" applies to the wall of the hub lumen 79 is sufficiently low to allow acceptable removal force. In an example embodiment the diameter of the unswollen tip 34' (reference FIG. 8A) is 0.060 inches, the diameter of the confined swollen tip 34" is 0.098 inches (the same diameter as the hub lumen 79), and the diameter of the unconfined swollen tip is 0.110 inches when placed in normal saline. However, these diameters will vary to match the diameter of the device that the cap is being used with. The preferred unconfined swollen diameter (defined as the diameter the tip will expand to if it is not confined by a lumen wall) is slightly larger than the diameter of the hub lumen 79. An additional beneficial effect of the swollen tip is that it produces a scrubbing effect on the catheter wall that will physically remove organisms adhered to the interior wall section upon removing the cap from the catheter.

In one embodiment, the tip is manufactured to produce anisotropic swelling, such that the diameter increases but the length does not substantially increase. In another embodiment the entire elongate member is made of an anisotropically swelling material such that the diameter increases but the length does not substantially increase.

In one implementation, the material of the tip 34" consists of a swellable polyurethane, such as Lubrizol TG-500, that has been heat fused onto the elongate member 33 which is a non-swellable polyurethane, such as Lubrizol 1065D. These materials provide acceptable swelling, durability, strength and flexibility. The elongate member is coated with antimicrobial agent in an amount sufficient to obtain an adequate antimicrobial effect, yet low enough to remain safe for the patient.

In reference to FIG. 9, this alternative embodiment of the invention is useful in applications where an elongate member will not fit into a catheter because the internal diameter of the catheter is too small, such as with peripherally inserted central catheters (PICC). In this embodiment, the cap 20 does not contain an elongate member as in previous embodiments. Instead, the cap has a luer end face 38 that is flat or slightly recessed, and the end face 38 is coated with an antimicrobial layer 39. The preferred type and amount of antimicrobial in the antimicrobial layer 39 is the same as the elongate member (reference the description for FIG. 5C). Similarly, the male luer 31 and the catheter threads 78 preferably contain the same type and amount of antimicrobial agent as the other embodiments. The antimicrobial agent is preferably applied to the end face using a precision metering pump with 15% chlorhexidine acetate in a methanol solution. Other solvent, percentages and coating methods may be used.

In reference to FIG. 10A, an alternative embodiment of the invention is shown in which the cap 20''' is manufactured from two components, a retaining ring 40''' and an insert 30. It is desirable to have a highly controlled and repeatable amount of antimicrobial agent placed upon the desired regions of the cap 20'''. It is also preferred to have different amounts of antimicrobial on the different regions. It becomes easier to coat each region of the cap 20''' if the retaining ring 40''' is not blocking access to the male luer 31 (and vice versa). This is accomplished by manufacturing the cap 20''' as two separate pieces, the retaining ring 40''' and the insert 30. The preferred amount of antimicrobial agent within each region remains the same as presented above (refer to Ref. 5C).

In reference to FIG. 10B, the insert 30 is coated with chlorhexidine acetate the elongate member 33 and along the male luer 31. The plate 32, cap shoulder 36, and the retaining flange 37 do not require coating. The two parts that are coated are the male luer 31 and the elongate member 33; contain the same amount of antimicrobial as referenced above.

In reference to FIG. 10C, the plate 32 at the proximal end of the insert 30 has a hole 35. The purpose of this hole 35 is to improve manufacturing. For instance, the hole 35 creates a convenient feature that can be used for holding and rotating the insert 30 to allow the part to be spun as it is being coated. The hole 35 also reduces shrinkage in the injected molded insert 30 by creating more uniform wall thickness.

In reference to FIG. 10D, the retaining ring 40''' is a commercially available product from Value Plastics, Inc. with the exception that the cap threads 41 are coated with an antimicrobial agent. The antimicrobial agent in the preferred embodiment is chlorhexidine acetate in the same preferred amount as disclosed above. The retaining ring 40''' is readily coated using a spraying technique where the retaining ring 40''' is spun along its axis, and the antimicrobial is sprayed directly onto the cap threads. As an alternative coating method, the cap threads 41 were coated by filling the internal portion of the ring 40''' with 7% chlorhexidine methanol solution, subsequently draining the solution and allowing the parts to dry. This resulted in approximately 1.2 mg of chlorhexidine acetate on the cap threads 41. The dose of antimicrobial may be adjusted by adjusting the solution concentration.

In reference to FIG. 10E, the retaining shoulder 46 comes into contact with the insert (not shown) when the insert is inserted inside the retaining ring 40'''. The proximal opening 43 is used to initially receive the insert 30 (refer to FIG. 10F) during assembly. The retaining fingers 45 are designed to retain the retaining ring 40''' onto the insert, as will be described in the reference below. The ring shoulder 46 helps secure the insert.

In reference to FIG. 10F, the preferred embodiment for the two-piece cap 20''' is shown. The insert 30 is shown fully inserted into the retaining ring 40'''. The tip 34 was pushed through the proximal opening until retaining ring 40''' bottomed out on the plate 32. The retaining fingers 45 are engaged with the retaining flange 37 to secure the retaining ring 40''' on the insert 30.

It is desirable to have the retaining ring 40''' not rotate freely on the insert 30. Instead, it is preferred to have the torque be greater than 0 pound-inches (lb-in) but less than 2.0 lb-in. In a more preferred embodiment, the torque is between 0.1 lb-in and 1.25 lb-in. In the most preferred embodiment, the torque is between 0.2 lb-in and 0.5 lb-in. By controlling the diameter of the insert shoulder 36 such that it interferes with ring shoulder 46, the torque can be controlled as shown in the graph depicted in FIG. 11.

It is preferred to keep the interference between the ring shoulder 46 and the insert shoulder 36 within the range of 0.002 inch and 0.009 inch in order to keep the rotation torque within an acceptable range.

Antimicrobial Agent

An antimicrobial agent can be incorporated both into the elongate member material and/or on the elongate member surface of the present invention. In a preferred embodiment, the antimicrobial agent is chlorhexidine acetate; approximately 250 µg of chlorhexidine acetate is coated onto a 17 mm long×1.9 mm diameter rod-shaped elongate member, resulting in a chlorhexidine acetate layer approximately 2 µm thick along. The luer portion is coated with 50 µg of chlorhexidine acetate, resulting in a layer that is approximately 0.4 µm thick. It is also possible to inject an antimicrobial agent into the catheter using a syringe, or to deliver antimicrobial agents by way of the connector tip cavity (dry dissolvable amount, applicable for Citrate or others requiring large amounts of antimicrobial agent).

The elongate member has the added benefit of displacing fluid from within the catheter as it is inserted, transferring the solution to the outer proximal region of the catheter connector (end face and treads). Antimicrobial agent from the cap dissolves into the displaced fluid, and thereby disinfecting the proximal end of the connector. Furthermore, when the fluid dries, it deposits a coating of chlorhexidine acetate or other appropriate antimicrobial on the connector as described above. As an alternative to using the elongate member, is the chlorhexidine acetate or other antimicrobial agent may be delivered by a coating on a luer tip (such as 250 µg of chlorhexidine acetate in a layer that is approximately 20 µm thick).

An antimicrobial composition is located on the outer surface of the elongate member, the male luer connector, and the retaining ring The antimicrobial composition elutes from the elongate member after insertion of the elongate member/ rod into a catheter. When the system is inserted into the catheter, the antimicrobial agent dissolves into the fluid contained within the catheter, thus coming into contact with infectious organisms that might be present along the connector surfaces and lumen wall of the catheter or in solution. Additionally, the antimicrobial agent and any infectious organisms are confined together in the small space along within the catheter. Another benefit is that the confining action of the clamp traps any infectious microbes within the catheter and prevents them from being transmitted to other areas of the catheter or to the body to prevent a systemic infection.

The antimicrobial agents should kill and/or provide stasis of Gram-positive and Gram-negative bacteria and fungi. The agents may also have efficacy at killing organisms within an established biofilm and/or degrading the extracellular matrix of the film. However, this is not necessary for the invention to be beneficial because the invention is designed to kill organisms before they have an opportunity to form a biofilm. The preferred antimicrobial agent is chlorhexidine acetate, also known as chlorhexidine diacetate. Other compounds containing chlorhexidine may be used (such as chlorhexidine free base, chlorhexidine gluconate and chlorhexidine with dyes). Chlorhexidine acetate has an advantage over chlorhexidine gluconate because the risks associated with para chloroaniline may be minimized. Other suitable antimicrobial agents may also be used. In general, the preferred antimicrobials are soluble in water, they have a history of clinical use with a demonstrated safety profile, they are antibiotic-free, they can be applied onto a medical device, and they can be subsequently dissolved into a composition having an effective concentration to inhibit growth of bacterial and fungal organisms. Suitable materials include tetrasodium ethylenediaminetetraacetic acid (tetrasodium EDTA), sodium citrate (yielding a concentration of 30% or higher), iodine, taurolidine, disodium EDTA, silver compounds (including silver nanoparticles and ions), silver sulfadiazine, and, triclosan.

While one particular drug or antimicrobial agent may provide relief from a wide range of challenging organisms that could potentially lead to catheter-related bloodstream infection, two or more agents may be used to increase efficacy against a broad range of infectious organisms (bacteria and fungi).

In particular, catheter-related infections arise from three broad classes of organisms: fungi, Gram-negative bacteria, and Gram-positive bacteria. If an antimicrobial agent can be identified that would abate one or two of these types of organisms, while this would certainly be beneficial, it would leave the patient vulnerable to the remaining type(s). By pairing agents with different modes of action, infections by an increased spectrum of organisms can be prevented. This synergy would likely lead to further decreases in catheter-related morbidity and mortality, lessening the impact of the implanted catheter on the patient's quality of life. The preferred combinations of antimicrobial agents are chlorhexidine acetate and EDTA, silver sulfadiazine and sodium dodecyl sulfate, and silver sulfadiazine and methylene blue.

Although treating, preventing, and eliminating infectious organisms for the prevention of infections is the primary use of the cap, ancillary benefits can also be envisioned which would involve incorporating additional agents. An anti-thrombotic agent eluting from the elongate member can be used to improve the action of the heparin used currently in the locking solution. An enzyme or agent which promoted degradation of the extra-cellular matrix of biofilm (generally composed of polysaccharides) could enable use of the cap for treatment as well as prevention.

In principle, antibiotics (rifampin, minocycline, etc.) can be incorporated into the cap or similar device and be as effective as non-antibiotic antimicrobials. However, continuous exposure to one antibiotic can lead to antibiotic resistant bacteria strains, for example, methicillin resistant *S. aureus* (MRSA). Therefore, the preferred embodiment uses an antimicrobial agent selected from the subset of those which are not antibiotics. If, for some reason, an antibiotic is used, the risk of developing antibiotic resistant strains of bacteria may be mitigated by preparing a second, complimentary, cap containing a different antibiotic. By using the two caps in an alternating fashion with successive dialysis treatments, infectious organisms that are resistant to one antibiotic may be killed by the other.

Experiments have been conducted to examine the performance of the preferred embodiment of the invention, which is called "Pursuit Vascular's ClearGuard HD" or the "ClearGuard HD". These experiments demonstrate that the ClearGuard HD is effective at substantially reducing organisms within catheters as intended. Two of the experiments are highlighted below.

In an experiment conducted at Pursuit Vascular, coated caps were effective at consistently transferring more than 50 µg of chlorhexidine acetate (also referred to as chlorhexidine diacetate) onto the catheter's threads with a single connection. Such transfer provides the catheter with a means of further reducing infection-causing organisms which is replenished with every use of the invention. 10 µg or more of chlorhexidine is effective at reducing bacteria and other infection-causing organisms at the threads, and further preventing the organisms from infiltrating the catheter's connector end face, luer and lumen. Chlorhexidine acetate has a wide safety profile when used outside the catheter where there is little risk of it entering the bloodstream. A preferred range of chlorhexidine on the cap threads is 100 µg to 2500 µg. 500 µg to 1200 µg is more preferred.

For instance, if using a chlorhexidine based antimicrobial, approximately 50 µg of chlorhexidine acetate can be effective in some embodiments. This was demonstrated in an experiment conducted at Pursuit Vascular in which 50 µg of chlorhexidine was coated on the cap's luer portion. The caps containing the coated luers killed all of the *Candida albicans* that were seeded within the catheter's luer region. Within the same experiment, the *Candida albicans* remained viable when uncoated caps were used. Greater than 5 µg chlorhexidine acetate on the luer region is effective; 10 µg to 300 µg is preferred, and 30 µg to 80 µg is most preferred.

Laboratory testing conducted for Pursuit Vascular, Inc. demonstrated that 250 µg of chlorhexidine acetate on the elongate member produces greater than a 10,000× reduction in number of infection-causing organisms when the cap is used in a standard hemodialysis catheters containing saline, heparin-saline, or saline with 4% sodium citrate. The safety profile of the invention can be enhanced by limiting the amount of chlorhexidine acetate available to enter the bloodstream, the preferred maximum amount of chlorhexidine acetate on the elongate member is 2000 µg, more preferred is 1000 µg, and most preferred is 350 µg.

Experiment 1

The objective of this experiment was to assess the antimicrobial effectiveness of Pursuit Vascular's ClearGuard HD device in the most difficult clinically-relevant model. Since the ClearGuard HD is intended to be placed in catheter hubs, but not extend into the extension tubing, the catheter model was chosen to be a female luer connector, extension tube and clamp. The total length of the female luer connector and the extension tubing was manufactured to maximize the length and volume that would be expected to be encountered clinically. *Candida albicans* (fungus) was chosen as the challenge microorganism, because in previous tests *Candida albicans* was shown to be the most challenging microorganism for the ClearGuard HD to eradicate. *Candida albicans* were added to three different lock solutions: heparin-serum, saline-serum, and SDB broth. These solutions represent the most relevant (and challenging) solutions that would be expected clinically. The catheters were filled with the lock solutions and *Candida albicans*, next the caps (either the ClearGuard HD or a standard cap) were secured, and then the catheters were incubated for approximately 46 hours to simulate the time between dialysis sessions. After incubation, the caps were removed and the lock solution was tested for the presence of organisms.

Experiment 1 results: The organism count is shown in FIG. 11 for ClearGuard HD caps and standard caps (shown as "with CGHD" and "without CGHD", respectively).

| Organism Count at Study End | | | |
|---|---|---|---|
| Solution | With CGHD | Without CGHD | Organism Reduction* |
| 5000 IU/ml Hep-Saline with 25% Serum | 0.0E+00 | 3.6E+06 | 3.6E+06 |
| Saline with 25% Serum | 0.0E+00 | 3.8E+03 | 3.8E+03 |
| SDB Broth | 0.0E+00 | 7.7E+08 | 7.7E+08 |

*Actual reduction in organism count is likely higher than calculated in this test because no organisms survived in the CGHD arm of the study.

The antimicrobial effectiveness of the ClearGuard HD was assessed against *Candida albicans*, the microorganism which has been the most difficult to eradicate when tested in a clinically relevant catheter model containing the most challenging and clinically relevant fluids.

All test samples using the ClearGuard HD had complete kill of the *Candida albicans*. In comparison, all control samples demonstrated growth of the CA. Since no *Candida albicans* survived during the ClearGuard HD portion of the test, the actual *Candida albicans* reduction may be significantly higher (better) than the sensitivity of this test. The minimum reduction of *Candida albicans*, when using the ClearGuard HD in place of a standard cap, was shown to be:

a. $3.6 \times 10^6$ CFU/ml for Heparin with 25% Serum b. $3.8 \times 10^3$ CFU/ml for Saline with 25% Serum c. $7.7 \times 10^8$ CFU/ml for SDB Broth This test demonstrates that the ClearGuard HD produces a significant reduction in *Candida albicans* within a clinically relevant catheter and with clinically solutions. *Candida albicans* was previously shown to be the most difficult organism to reduce of the other clinically relevant microorganisms tested, therefore concluding that the ClearGuard HD produces broad-spectrum reduction in clinically relevant microorganisms.

Experiment 2

The objective of this experiment was to assess the relative rate of microorganism contamination in hemodialysis catheter lumens when using the ClearGuard HD versus standard caps in a simulated clinical environment. This experiment was intended to examine the effectiveness of the ClearGuard HD at preventing microorganism contamination of hemodialysis catheter lumens (both proximal and distal to the extension tubing clamp), compared to standard caps in a simulated clinical environment. Growth media was used inside of the catheter instead of the standard locking solution in order to provide an extremely sensitive means of detecting whether any microorganisms entered inside the catheter.

The primary route for infections-causing microorganisms to enter and colonize a hemodialysis (HD) catheter is generally accepted to be through the catheter's hub. During clinical use, hemodialysis catheter hubs are routinely exposed to microorganisms because the catheter and hub lies against the patient's skin. All commercially available catheter caps are primarily designed to keep fluid inside the catheter lumen but they are not well designed for preventing microorganisms from reaching and colonizing catheter lumens.

In order to compare whether the rate of microorganism colonization is affected by cap type (ClearGuard HD versus standard cap), twenty identical catheters were affixed to clothing, in a manner that would keep the catheters in contact with human skin, which occurs during clinical use. The catheters were kept in contact with the skin for a maximum of 26 days. Once a catheter's lumen was determined to be contaminated, the catheter was allowed to be removed from the study. The test consisted of two arms: 1) the ClearGuard HD arm, and 2) the standard cap arm. Except for the cap type used, the two arms were identical in all other ways (i.e., identical catheters, solutions, handling, etc.).

The study was designed to mimic the hemodialysis clinical practice as closely as practical. The entire volume of lock solution, including the solution distal to the clamp, was included in the microbiological testing to ensure with high probability that if any microorganisms were present anywhere within the catheter that they would be detected. Standard microbiological techniques were used to test for the presence of organisms.

The number of catheters that remained free from microorganism contamination as time progressed is illustrated in FIG. 13 below. Within fourteen days, all catheters using standard caps had become contaminated, while none of the catheters using the ClearGuard HD had become contaminated throughout the full twenty-six days of the experiment.

This experiment showed that, when catheters were filled with a growth media, were worn to simulate actual patient end use and were subjected to a standard dialysis fluid exchange schedule, the catheters using standard caps became contaminated with microorganisms at a mean time to failure of 8.9 days, and all of these catheters (10 out of 10) became contaminated by 14 days. In comparison, none of the catheters using the ClearGuard HD (0 out of 10) became contaminated throughout the entire 26 day test. The ClearGuard HD performs significantly better than standard caps (the current standard of care) at reducing microorganism contamination inside of catheters in a simulated clinical environment. While the invention has been particularly shown and described as referenced to the embodiments thereof, those skilled in the art will understand that the foregoing and other changes in form and detail may be made therein without departing from the spirit and scope of the invention.

The following is claimed:

1. An antimicrobial cap that is configured to disinfect a medical connector or catheter when the antimicrobial cap is inserted into a channel containing a liquid in the medical connector or catheter, the antimicrobial cap comprising:

an outer shroud having a threaded portion positioned on an interior surface thereof; and an elongate portion integral with a sealing portion of the antimicrobial cap, the sealing portion is coupled to the outer shroud, the elongate portion being entirely distal to the outer shroud and having a length extending along a longitudinal axis of the antimicrobial cap that is greater than a length of the sealing portion of the antimicrobial cap measured along the longitudinal axis, the elongate portion having a solid cross-section at a distal tip of the elongate portion; and a water-soluble dry antimicrobial agent on at least an outside surface of the elongate portion;

wherein:

the antimicrobial cap is configured so that, as the elongate portion is inserted into the channel in the medical connector or catheter, at least some of the water-soluble dry antimicrobial agent is transferred from the elongate portion of the antimicrobial cap into the liquid in the medical connector or catheter, and at least some of the liquid in the medical connector or catheter is displaced to flow out of a proximal opening of the medical connector or catheter and onto an exterior surface of the medical connector or catheter; and the threaded portion is configured to attach to an outside surface of the medical connector or catheter.

2. The antimicrobial cap of claim 1, wherein the sealing portion includes a tapered region.

3. The antimicrobial cap of claim 1, wherein the water-soluble dry antimicrobial agent comprises chlorhexidine.

4. The antimicrobial cap of claim 1, further comprising a shoulder integrally formed with and proximal to the sealing portion.

5. The antimicrobial cap of claim 1, wherein the outer shroud has retaining fingers that engage with a retaining flange attached to the sealing portion.

6. The antimicrobial cap of claim 1, wherein the elongate portion has a solid cross-sectional region at a proximal end.

7. The antimicrobial cap of claim 1, wherein the entire elongate portion has a solid cross section.

8. A combination, comprising:
the antimicrobial cap of claim 1; and
the medical connector or catheter.

9. An antimicrobial cap that is configured to disinfect a medical connector or catheter when the antimicrobial cap is inserted into a channel containing a liquid in the medical connector or catheter, the antimicrobial cap comprising:
an outer shroud having a threaded portion positioned on an interior surface thereof;
an elongate portion integrally formed with a first portion of the antimicrobial cap, the first portion is coupled to the outer shroud, the elongate portion extending along a longitudinal axis and being entirely distal to the outer shroud, wherein a length of the elongate portion is greater than a length of the first portion of the antimicrobial cap taken along the longitudinal axis, wherein the elongate portion has a solid cross-sectional region at a distal end; and
a water-soluble dry antimicrobial agent applied along a portion of the elongate portion in a location that is configured to contact the liquid when the antimicrobial cap is inserted into the medical connector or catheter;
wherein:
the antimicrobial cap is configured so that, as the elongate portion is inserted into the channel in the medical connector or catheter, at least some of the water-soluble dry antimicrobial agent is transferred from the elongate portion of the antimicrobial cap into the liquid in the medical connector or catheter, and at least some of the liquid in the medical connector or catheter is displaced to flow out of a proximal opening of the medical connector or catheter and onto an exterior surface of the medical connector or catheter; and
the threaded portion is configured to attach to an outside surface of the medical connector or catheter.

10. The antimicrobial cap of claim 9, wherein the first portion of the antimicrobial cap includes a tapered region.

11. The antimicrobial cap of claim 9, wherein the elongate portion has a solid cross-sectional region at a proximal end.

12. The antimicrobial cap of claim 9, wherein the first portion of the antimicrobial cap includes a tapered male luer extending along the longitudinal axis from a proximal portion of the antimicrobial cap, wherein the tapered male luer is shorter than the elongate portion.

13. The antimicrobial cap of claim 9, wherein the outer shroud comprises a shoulder configured to secure the elongate portion.

14. The antimicrobial cap of claim 9, wherein the first portion of the antimicrobial cap includes a shoulder extending along the longitudinal axis from a proximal portion of the antimicrobial cap.

15. The antimicrobial cap of claim 9, wherein the outer shroud has retaining fingers that engage with a flange attached to the first portion of the antimicrobial cap.

16. The antimicrobial cap of claim 9, wherein the entire elongate portion has a solid cross section.

17. A combination, comprising:
the antimicrobial cap of claim 9; and
the medical connector or catheter.

18. An antimicrobial cap that is configured to disinfect a medical connector or catheter when the antimicrobial cap is inserted into a channel containing a liquid in the medical connector or catheter, the antimicrobial cap comprising:
an outer shroud having a threaded portion along an interior surface thereof, the outer shroud having a proximal opening and a distal opening;
a proximal plate coupled to a tapered male luer base, the proximal plate formed separately from the outer shroud, the proximal plate covering the proximal opening;
an elongate rod sized to fit into the medical connector or catheter, the elongate rod extending from the tapered male luer base, the elongate rod having a solid cross-section at a distal tip; and
a water-soluble dry antimicrobial agent on at least an outside surface of the elongate rod;
wherein:
the antimicrobial cap is configured so that at least a portion of the elongate rod extends beyond the distal opening of the outer shroud;
the antimicrobial cap is configured so that, as the elongate rod is inserted into the channel in the medical connector or catheter, at least some of the water-soluble dry antimicrobial agent is transferred from the elongate rod of the antimicrobial cap into the liquid in the medical connector or catheter, and the tapered male luer base is configured to create a fluid tight seal with an inner wall of the medical connector or catheter, and at least some of the liquid in the medical connector or catheter is displaced to flow out of a proximal opening of the medical connector or catheter and onto an exterior surface of the medical connector or catheter; and
the threaded portion of the outer shroud is configured to attach to an outside surface of the medical connector or catheter.

19. The antimicrobial cap of claim 18, wherein the elongate rod has a solid cross-sectional region at a proximal end.

20. A combination, comprising:
the antimicrobial cap of claim 18; and
the medical connector or catheter.

\* \* \* \* \*